(12) United States Patent
Sidhu et al.

(10) Patent No.: US 8,940,295 B2
(45) Date of Patent: Jan. 27, 2015

(54) PURIFICATION AND ISOLATION OF RECOMBINANT OXALATE DEGRADING ENZYMES AND SPRAY-DRIED PARTICLES CONTAINING OXALATE DEGRADING ENZYMES

(71) Applicant: Oxthera Intellectual Property AB, Stockholm (SE)

(72) Inventors: Harmeet Sidhu, Gainesville, FL (US); Aaron Blake Cowley, Gainesville, FL (US); Carl-Gustaf Golander, Uppsala (SE); Qingshan Li, Gainesville, FL (US)

(73) Assignee: Oxthera Intellectual Property AB, Stockholm (SE)

( * ) Notice: Subject to any disclaimer, the term of this patent is extended or adjusted under 35 U.S.C. 154(b) by 0 days.

(21) Appl. No.: 13/851,594

(22) Filed: Mar. 27, 2013

(65) Prior Publication Data
US 2013/0216515 A1    Aug. 22, 2013

Related U.S. Application Data

(62) Division of application No. 12/497,275, filed on Jul. 2, 2009, now Pat. No. 8,431,122.

(51) Int. Cl.
| | |
|---|---|
| A61K 38/00 | (2006.01) |
| A61K 38/54 | (2006.01) |
| A61K 38/44 | (2006.01) |
| C12N 9/88 | (2006.01) |
| C12N 9/10 | (2006.01) |
| C12N 9/06 | (2006.01) |
| C07H 21/04 | (2006.01) |
| A61K 38/51 | (2006.01) |
| A61K 9/16 | (2006.01) |

(52) U.S. Cl.
CPC ......... *A61K 38/51* (2013.01); *C12Y 401/01002* (2013.01); *A61K 9/1635* (2013.01)
USPC ........ 424/94.5; 424/94.2; 424/94.4; 435/232; 435/193; 435/191; 536/23.2

(58) Field of Classification Search
CPC . A61K 2300/00; A61K 38/00; A61K 31/785; A61K 38/54; C12N 9/88; C12N 11/04; C12N 11/06; C12N 15/8257; C12N 9/00; C12N 11/00; C12N 11/08; C12Q 1/527; C12Y 401/01002; C12Y 304/23002; A23K 1/1653
See application file for complete search history.

(56) References Cited

U.S. PATENT DOCUMENTS

| | | | |
|---|---|---|---|
| 5,427,935 A | 6/1995 | Wang et al. | |
| 6,200,562 B1 | 3/2001 | Allison et al. | |
| 6,355,242 B1 | 3/2002 | Allison et al. | |
| 6,699,469 B2 | 3/2004 | Allison et al. | |
| 6,929,940 B1 | 8/2005 | Richards et al. | |
| 8,431,122 B2 | 4/2013 | Sidhu et al. | |
| 8,486,389 B2 | 7/2013 | Sidhu | |
| 2007/0178070 A1 | 8/2007 | Kaul et al. | |
| 2007/0184118 A1 | 8/2007 | Li et al. | |
| 2010/0028422 A1 | 2/2010 | Kaul et al. | |
| 2011/0002906 A1 | 1/2011 | Sidhu et al. | |
| 2012/0189604 A1 | 7/2012 | Sidhu et al. | |

FOREIGN PATENT DOCUMENTS

| | | |
|---|---|---|
| WO | WO 2005/123116 A2 | 12/2005 |
| WO | WO 2008/105911 A2 | 9/2008 |

OTHER PUBLICATIONS

Office Action issued on Oct. 1, 2013 in U.S. Appl. No. 13/381,430 (US 2012/0189604).
International Search Report issued on Nov. 15, 2010 in application No. PCT/EP2010/003864.
European Search Report issued on Sep. 4, 2009 in application No. EP 09 16 4430.
U.S. Appl. No. 11/899,018, filed Aug. 31, 2007.
Khan et al., "A pH-Dependent Colon-Targeted Oral Drug Delivery System Using Methacrylic Acid Copolymers. II. Manipulation of Drug Release Using Eudragit® L100 and Eudragit S100 Combinations," Drug Development and Industrial Pharmacacy, vol. 26, No. 5, pp. 549-554, 2000.
Aoki et al., "Purification of Recombinant Human Pepsinogens and Their Application as Immunoassay Standards," Biochemistry and Molecular Biology International, vol. 45, No. 2, pp. 289-301, Jun. 1998.
Svedruzic et al., "The enzymes of oxalate metabolism: unexpected structures and mechanisms," Archives of Biochemistry and Biophysics, vol. 433, No. 1, pp. 176-192, 2005.
Svedruzic, Mechanism of the reaction catalyzed by the oxalate decarboxylase from *Bacillus subtilis*, A dissertation for Ph.D., pp. 1-102, University of Florida, 2005.
Office Action issued on Apr. 4, 2011 by the Examiner in U.S. Appl. No. 12/497,275 (US 2011/0002906).
Office Action issued on Sep. 29, 2011 by the Examiner in U.S. Appl. No. 12/497,275 (US 2011/0002906).
Office Action issued on May 11, 2012 by the Examiner in U.S. Appl. No. 12/497,275 (US 2011/0002906).
Notice of Allowance issued on Dec. 20, 2012 by the Examiner in U.S. Appl. No. 12/497,275 (US 2011/0002906).

*Primary Examiner* — Iqbal H Chowdhury
(74) *Attorney, Agent, or Firm* — Foley & Lardner LLP

(57) ABSTRACT

The present invention comprises methods and compositions for the reduction of oxalate in humans, and methods for the purification and isolation of recombinant oxalate reducing enzyme proteins. The invention provides methods and compositions for the delivery of oxalate-reducing enzymes in particle compositions. The compositions of the present invention are suitable in methods of treatment or prevention of oxalate-related conditions.

20 Claims, 2 Drawing Sheets

PURIFICATION AND ISOLATION OF RECOMBINANT OXALATE DEGRADING ENZYMES AND SPRAY-DRIED PARTICLES CONTAINING OXALATE DEGRADING ENZYMES

FIELD OF THE INVENTION

The present invention relates to spray-dried particles comprising oxalate reducing enzymes for delivering the enzymes in an active form to the stomach, where the oxalate reducing enzymes exert their effect. Thus, the present invention provides means for reducing oxalate in the stomach. Moreover, the present invention relates to a method for isolating a recombinant protein that is insoluble in the cytoplasm of a host cell and is not found as an inclusion body, which is regarded as inactive, mis-folded protein precipitate, comprising,
a) separating an insoluble recombinant protein not found as an inclusion body from soluble host cell proteins; and
b) solubilising the separated recombinant protein.

BACKGROUND OF THE INVENTION

Kidney/urinary tract stone disease (urolithiasis) is a major health problem throughout the world. Most of the stones associated with urolithiasis are composed of calcium oxalate alone or calcium oxalate plus calcium phosphate. Other disease states have also been associated with excess oxalate. These include, vulvodynia, oxalosis associated with end-stage renal disease, cardiac conductance disorders, Crohns's disease, and other enteric disease states.

Oxalic acid, and/or its salts, oxalate, is found in a wide variety of foods, and is therefore, a component of many constituents in human and animal diets. Increased oxalate absorption may occur after foods containing elevated amounts of oxalic acid are eaten. Foods such as spinach and rhubarb are well known to contain high amounts of oxalate, but a multitude of other foods and beverages also contain oxalate. Because oxalate is found in such a wide variety of foods, diets that are low in oxalate and which are also palatable are hard to formulate. In addition, compliance with a low oxalate diet is often problematic.

The risk for formation of kidney stones revolves around a number of factors that are not yet completely understood. Kidney or urinary tract stone disease occurs in as many as 12% of the population in Western countries and about 70% of these stones are composed of calcium oxalate or of calcium oxalate plus calcium phosphate. Some individuals (e.g. patients with intestinal disease such as Crohn's disease, inflammatory bowel disease, or steatorrhea and also patients that have undergone jejunoileal bypass surgery) absorb more of the oxalate in their diets than do others. For these individuals, the incidence of oxalate urolithiasis increases markedly. The increased disease incidence is due to increased levels of oxalate in kidneys and urine, and this, the most common hyperoxaluric syndrome in humans, is known as enteric hyperoxaluria. Oxalate is also a problem in patients with end-stage renal disease and there is recent evidence that elevated urinary oxalate is also involved in vulvar vestibulitis (vulvodynia).

Enteric coated or other compositions comprising oxalate reducing bacteria have been suggested for reducing oxalate concentrations during passage through the intestines before being absorbed systemically. Enteric coated compositions pass through the stomach in intact form, i.e. the coating is intact and accordingly, oxalate will not be degraded in the stomach. A better approach is to reduce oxalate in the stomach before it is absorbed in the intestines. Accordingly, there is a need for developing compositions that enable reduction of oxalate in the stomach in order to reduce, for example, dietary oxalate. Moreover, such compositions are suitable for use in the treatment of enteric and absorptive hyperoxalurias such as hyperoxalurias causing recurrent stone disease. An objective with such a treatment is for the patients to have normal or at least lowered urinary oxalate levels.

SUMMARY OF THE INVENTION

The present invention relates to spray-dried particles comprising an oxalate degrading enzyme. The spray-dried particles are suitable for use in pharmaceutical and/or food compositions for delivering the enzyme in an active form to the stomach and to degrade oxalate in the stomach. Thus, the present invention also provides methods for treating and preventing oxalate-related conditions by administration of the spray-dried particles or compositions comprising them.

The present invention also provides a method for isolation and purification of recombinant proteins that are insoluble or only slightly soluble in the cytoplasm of a host cell, and are not found as inclusion bodies of the host cell. Notably, the recombinant proteins are recombinant oxalate degrading enzymes.

DETAILED DISCLOSURE OF THE INVENTION

Figure 1:
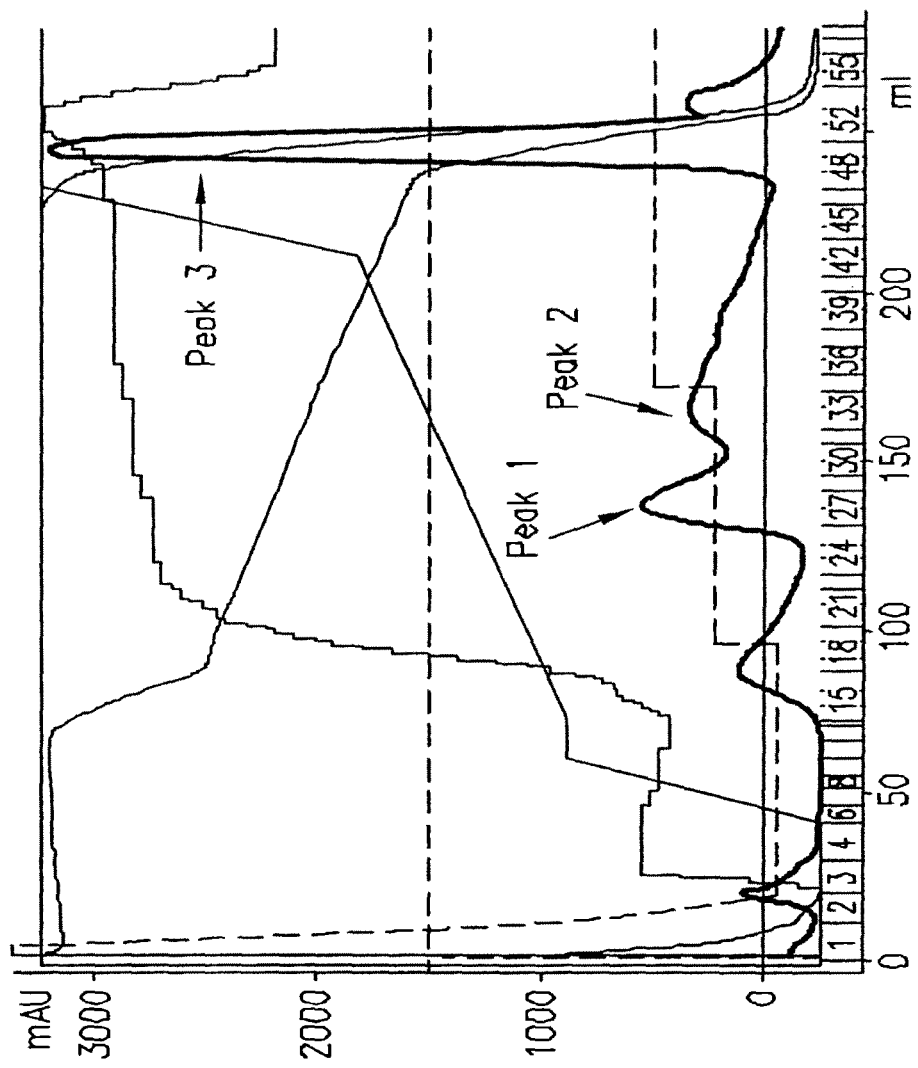
FIG. 1 is a chromatogram of wild type OxDC eluted from Phenyl-sepharose column by segment gradient salt elution. Peaks 1 and 2 both contain OxDC, but peak 1 contains 80-90% of OxDC with higher specific activity (50-60 U/mg pure OxDC) and peak 2 contains 30-70% OxDC with lower specific activity (30-50 U/mg pure OxDC). OxDC in peak 2 is theorized to be damaged or folded incorrectly. Peak 3 is impurities.

As appears from the above, the present invention provides
i) a method for isolating and purification of recombinant proteins, notably oxalate degrading enzymes,
ii) spray-dried particles comprising one or more oxalate degrading enzymes, and
iii) compositions comprising such particles.

Thus, the present invention is further developments of previously described compositions and method for treating oxalate-related diseases see e.g. WO 2007/075447 (to the same Applicant). Moreover, the present inventors have surprisingly found that specific mutations of the wild-type oxalate decarboxylase, notably by substituting a cysteine residue in position 383 with serine, alanine or arginine, confer physico-chemical properties to the enzyme that are particularly advantageous in the isolation and purification of the enzyme. Thus, the present isolation and purification method involves fewer steps than normally seen and makes use of variations in solubility of the enzymes in cytoplasma and in purification media.

Furthermore, the present inventors have found a more simple solution to deliver active oxalate degrading enzymes to the stomach. In WO 2007/075447 (to the same Applicant) compositions are described that contain particles having a content of an oxalate degrading enzymes. The particles contain a combination of various polymers and are protected by the harsh environment in the stomach by multiple layers of polymers and/or by cross-linking the polymers to strengthen the resistance towards pepsin and pH in the stomach. However, a more simple solution has been developed that makes use of a very specific group of polymers, notably poly(meth) acrylates, in combination with one or more oxalate degrading enzymes. The particles are prepared using a mild process, namely spray-drying. Even if the enzymes may not be completely protected from the environment in the stomach by incorporating them into spray-dried particles, the examples herein show a remarkable activity after the spray-drying method and after exposure to a simulated gastric environment.

DEFINITIONS

The term "oxalate reducing enzyme" as used herein is intended to denote any enzyme that is capable of reducing oxalate. It may reduce oxalate per se and/or it may function in an oxalate reduction pathway. In this context the term "oxalate" encompasses oxalic acid and/or any salts(s) thereof (oxalate). The present invention contemplates the use of any known oxalate reducing or degrading enzymes.

Enzymes used in the particles, compositions and methods of the present invention include, but are not limited to, oxalate oxidase, oxalate decarboxylase (abbreviated OxDc), oxalyl-CoA decarboxylase, or formyl-CoA transferase, or combinations thereof, whether native or mutated. Moreover, other enzymes, cofactors and co-enzymes that are substituents of oxalate degradation pathways or involved in oxalate metabolic pathways, particularly oxalate reduction, are also of relevance alone or in combination with one or more of the above-mentioned enzymes. In the present context not only the enzymes are encompassed by this definition, but also polynucleotide sequences that encode oxalate-reducing genes and proteins are contemplated by the present invention. The present invention also contemplates any binding partners of these enzymes and includes antibodies and antibody fragments that bind to or interact with the enzymes.

The enzymes may be derived by isolation from organisms, they may be purified, they may be made synthetically, semi-synthetically or by recombinant means, or they may be used as a cell lysate. Normally, the enzymes will be employed as purified recombinant proteins. When used in a medical use (as a drug) or in food (as food supplement, functional food or as a prophylactic measure), it is preferred that the one or more enzymes used are well-defined with respect to purity and activity.

One or more enzymes, mutated or wild-type, from the three main classes of oxalate-degrading enzymes are generally employed. Oxalate oxidase, is expressed in higher plants and catalyzes the oxygen dependent oxidation of oxalate to $CO_2$ with concomitant formation of $H_2O_2$. This reaction forms the basis of current assays for the detection of urinary oxalate levels. A rOxOx three-step purification procedure has been developed to obtain oxalate oxidase from barley roots. This enzyme is also present in beetroot stem and root, amaranthus leaves, sorghum and many other grains.

Oxalate decarboxylase (EC 4.1.1.2), the second class of oxalate metabolizing enzymes, is mainly present in fungi. It has been reported and characterized in several fungi such as, *Myrothecium verrucaria*, certain strains of *Aspergillus niger*, white rot fungus, *Coriolus versicolor* and *Collybia velutipes*. This enzyme converts oxalate to formate and carbon dioxide in an oxygen dependent reaction. Oxalate decarboxylases also have been used in the clinical assay of oxalate in blood and urine and can be used to lower oxalate levels in foods and the environment. The YvrK protein (the *B. subtilis* oxalate decarboxylase) has been expressed as a functional recombinant protein in *E. coli*, purified to homogeneity and fully characterized.

Oxalyl-CoA decarboxylase is active on the CoA-activated substrate and converts it into formyl-CoA. A formyl-CoA transferase then acts to exchange formate and oxalate on CoA. These enzymes have been studied in the oxalate reducing bacteria, *Pseudomonas oxalaticus* commonly found in the soil and in *Oxalobacter formigenes*, residing in the GI tract of vertebrates and humans. The enzymes have been fully reviewed in, "The enzymes of oxalate metabolism: Unexpected structures and metabolism" Svedruzic D. at al. *Arch Biochem Biophys*. 2005 Jan. 1; 433(1):176-92, which is herein incorporated in its entirety. The enzymes, whether native enzymes, isolated proteins or those made by recombinant techniques, may be modified by recombinant or chemical means and may contain side groups or other appended molecules. For example, enzymes may be modified to have linker molecules for attachment to other molecules or chemical compounds.

As appears from the examples herein specific mutations of oxalate decarboxylase that lead to a replacement amino acid for cysteine 383 are advantageous (e.g. C383S, C383A, C383R). Accordingly, such recombinant enzymes are specifically of interest in the various aspects of the present invention.

As used herein the singular of the term "an enzyme" refers to multiple copies of the enzyme molecule, as is commonly understood in reference to protein molecules.

As used herein, enzyme includes recombinant enzyme proteins.

As used herein, the term "one or more enzymes" means that one type of enzyme may be present, such as formyl-CoA transferase is intended, or more than one type of enzyme, such as a composition comprising, for example oxalyl CoA decarboxylase and formyl CoA transferase; oxalate decarboxylase and oxalate oxidase, or a combination of wild-type enzyme and mutant enzyme, are present in the composition.

The term "inclusion body" (which also could be denoted "protein inclusion body" or "cytoplasmic inclusion body" means a body formed by aggregation of insoluble polypeptide chains that is found in the cytoplasma of cells. Such inclusion bodies are seen in prokaryotic cells that serve as hosts for recombinantly produced foreign proteins. It is currently believed that the majority of the recombinant proteins in inclusion bodies are misfolded or biologically inactive, though some activity has been seen in recombinantly produced fluorescent proteins. As is apparent from the above, the invention does not relate to recombinant proteins found as inactive inclusion bodies when expressed in a host such as e.g. *E. Coli* and consequently, the invention relates to recombinant enzymes that are expressed and resulting in such a folded state so as to enable enzymatically active forms.

The term "particles", is used herein to describe compositions containing one or more types of an oxalate-reducing enzyme combined with a polymer. In general the term "particles", is used as the broadest term, i.e. without any specific size or shape attribution.

The term "spray-dried particles" mean particles that are obtained by a spray-drying method.

It must be noted that, as used in this specification and the appended claims, the singular forms "a", "an", and "the" include plural referents unless the context clearly dictates otherwise.

Method for Isolating and Purification of Recombinant Proteins, Notably Oxalate Degrading Enzymes The present invention provides a method for isolation and purification of recombinant proteins from host cells. The method comprises purifying oxalate reducing enzymes using efficient and simplified steps that result in improved yields of protein.

Recombinant proteins may include mutated oxalate reducing enzymes. The methods of the present invention are directed to recombinant proteins that are present in the cytoplasm of a host cell as active enzyme proteins, which are not soluble in the cytoplasm and appear to be precipitated, but are not found as inclusion bodies. Such proteins are thought to be insoluble or only slightly soluble in the cytoplasm of the host cell. An aspect of the present invention comprises lysis of the host cell and facilitated separation of the recombinant protein from the soluble cytoplasmic proteins. Separation may easily be accomplished by centrifugation or filtration of the cytoplasm. After separation, the recombinant protein is preferentially solubilized by methods including, but not limited to, adding binding ligands or altering the pH. Once soluble, the protein can be removed from solution, for example by precipitation, and stored or used, such as in particles disclosed herein.

Methods of the present invention comprise methods for isolation and purification of recombinant oxalate reducing enzymes, such as mutated recombinant oxalate reducing enzyme proteins. Expression of recombinant proteins often results in the sequestering of the proteins in inclusion bodies in $E.$ $coli$ because the proteins in inclusion bodies pose much less of a toxic burden to the host cells than soluble recombinant proteins. The proteins in inclusion bodies are also less accessible to degradation by $E.$ $coli$ proteases due to the insoluble form. However, it is quite challenging to refold the proteins from inclusion bodies to yield active enzymes. If a protein can be expressed in an active form, but insoluble or only slightly soluble in $E.$ $coli$ cells during expression, and are not found as inclusion bodies, the protein expression could be at levels like those seen when inclusion bodies are formed. Proteins having limited solubility in the cytoplasm and thus, precipitating in the cytoplasm of the cells, would not require a refolding step.

For example, oxalate decarboxylase (OxDC) wild type recombinant protein has a certain level of solubility in $E.$ $coli$ cytoplasm, with a smaller portion (5%, Table 1) found as soluble protein in cell lysate and a larger portion (95%, Table 1) found as insoluble protein in the broken cell pellet. The insoluble portion can dissolve in high salt concentrations such as 1M NaCl or 0.75M $(NH_4)SO_4$ and the dissolved OxDC contains two major forms which can be separated by a hydrophobic interaction chromatography (HIC) column (FIG. 1). Both OxDC peaks are active, but OxDC in the peak eluted at higher concentrations of salt (peak 1, FIG. 1) shows about 20% higher specific activity. It appears that the OxDC in the peak eluted at lower concentrations of salt (peak 2, see FIG. 1) is damaged. This protein fraction is more hydrophobic and less active. Soluble proteins in the cytoplasm are more accessible to damage by protease hydrolysis, other enzyme catalyzing reactions, chemical reaction and physical modification.

Proteins expressed as inclusion bodies have been widely reported, but there is no report on how to express a protein in an insoluble or slightly insoluble state, such as precipitated, and in an active form. Having a recombinant protein rendered less soluble in the cytoplasm of the host leads to a simplified purification method for the protein. Because the recombinant protein is insoluble or has lower solubility, the soluble proteins of the host organism, such as $E.$ $coli$, are easily separated by centrifugation or filtration, generally as a first step after lysis of the host cell. The insoluble or slightly soluble recombinant protein, found in the centrifugation pellet or the remainder after filtration, may be treated, such as by solubilization with a selective buffer. A selective buffer is found by selection of pH and/or screening specific binding ligands. Many proteins have very limited solubility when the pH is close to the pI, but have increased solubility when the pH is greater than 2 pH units above or below the pI. Protein solubility may also be changed by suspending the pellet in solutions containing binding ligands. For example, OxDC has limited solubility at pH 4.5-7.8 for the wild type recombinant protein and pH 4.0-8.0 for the C383S mutant protein. C383 indicates the cysteine at amino acid 383 in the oxalate decarboxylase amino acid sequence. The S indicates that the cysteine has been replaced with a serine. OxDC solubility increases if the pH is greater than 8.5 for the wild type OxDC and 9.0 for the C383S mutant. Tris and arginine are selective binding ligands to OxDC, and use of either of them will increase OxDC solubility. Methods of the present invention comprise purification steps comprising adding binding ligands or changing the pH of the media to aid in solubility of enzymes or proteins found in a pellet after centrifugation, or retentate after filtration, of soluble protein of a host cell.

Moreover, such methods for isolating a mutated oxalate reducing enzyme recombinant protein may result in increased amounts of recovered protein, and higher amounts than those seen with recombinant wild-type oxalate reducing enzyme protein. The methods normally also have fewer steps so that a more simple purification process is possible. For example, the soluble proteins of the host organism, such as $E.$ $coli$, are separated, such as by centrifugation or filtration from the recombinant protein which is insoluble or has lower solubility than the host proteins in the host cell cytoplasm. Mutated oxalate reducing recombinant proteins may not be like the wild-type recombinant protein in other ways, such as the mutated proteins may not form protein-protein interactions that lead to aggregate formations. For example, replacement of the cysteine amino acid in oxalate decarboxylase results in a mutated protein that cannot form disulfide bonds, which leads to fewer to no protein aggregates.

An example of a method of the present invention comprises lysis of host cells that are making recombinant mutated oxalate reducing enzyme protein or proteins. After lysis of the host cells, for example, $E.$ $coli$ cells, all soluble host proteins are removed, for example, by filtration or centrifugation. The recombinant protein, such as a mutant recombinant oxalate reducing enzyme protein, which is not soluble or only slightly soluble in the cytoplasm of the host cell, and is not found as an inclusion body, is found in the centrifugation pellet or as retentate in filtration. The mutant protein is then solubilized, such as by solubilization with a selective buffer or a binding ligand, or other methods known to those skilled in the art. A selective buffer may be determined for example, by pH parameters. Many proteins have limited solubility when the pH is close to the pI, but will have increased solubility when the pH is greater than 2 pH units above or below the pI. For example, OxDC has limited solubility at pH 4.5-7.8 for the wild type recombinant protein and pH 4.0-8.0 for the C383S mutant recombinant protein.

Solubilization may also be affected by protein binding ligands. Protein solubility may change when binding ligands are present in solution. This property can be applied to protein purification through selective precipitation and dissolving. Binding ligands for a particular protein can be found by methods known to those skilled in the art, such as differential scanning calorimetry, UV spectroscopy, infrared spectroscopy, fluorescence spectroscopy and other methods which detect ligands and protein interactions. For example, there are a number of chemical compounds and ions that can bind to OxDC and influence solubility such as Tris, arginine, $Mn^{2+}$, $Mg^{2+}$, and $Ca^{2+}$. It is preferable to use compounds or ions that do not inhibit the activity of the enzyme or if the compounds or ions inhibit activity that the compounds or ions are easily removed to recover active enzyme proteins. For example, Tris and arginine do not inhibit OxDC activity and increase OxDC solubility when pH is greater than 8.0 for wild type OxDC and 8.5 for the C383S mutant of OxDC.

Methods of the present invention for isolation and purification of a mutant recombinant oxalate reducing enzyme protein may comprise one or both of, low solubility of the recombinant mutant protein in host cytoplasm, and high solubility of the mutant recombinant oxalate reducing enzyme protein after changing solubilization conditions such as by adding binding ligands and/or adjusting pH.

In currently used processes for isolating and purifying recombinant proteins problems often arise in the use of large chromatography columns which are challenging to construct and operate at a scale that is required for large scale isolation and purification. This process is demonstrated in Example 1. Eliminating such steps would lead to a lower cost for purification and a simpler process, which is demonstrated in Example 4.

Methods of the present invention comprise purification or isolation of a recombinant protein from host cells. Methods of isolation comprise isolating a recombinant protein that is slightly insoluble to insoluble in the cytoplasm of the host organism. Isolation steps comprise obtaining a host cell lysate, washing the lysate, such as by resuspending the lysate and centrifuging it to form a lysate pellet; suspending the lysate pellet in a protein solubilization media, such as a media that contains binding ligands or other compounds that alter the pH response of the protein (e.g. increase the solubility of the protein); centrifuging the mixture and acting on the liquid phase, not the non-soluble pellet. The recombinant protein is removed from the liquid phase. For example, the pH of the liquid phase is adjusted and the recombinant protein precipitates out of solution. The non-soluble pellet may be re-extracted multiple times to form liquid phases out of which the recombinant protein is removed, such as by precipitation. The removed protein may be washed one or more times and stored or used as needed.

Enzymes that are insoluble or only slightly soluble in the cytoplasm and are not found as an inclusion body of host cells, such as *E. coli*, and are isolated by the methods taught herein, may comprise recombinant non-native or mutated oxalate reducing enzyme proteins that comprise modifications or mutations, including, but not limited to, chimeras formed using domains comprising the oxalate reducing active site of an oxalate reducing enzyme, or peptide fragments, notably those comprising or consisting of the active sites; modifications or mutations, including, but not limited to, deletions, insertions, replacements, reversions, mutations for increased activity, substitution of naturally occurring amino acids with non-natural amino acids, or other modifications known to those skilled in the art. Such modified enzymes may have more, less or the same activity as native enzymes, or may have characteristics that are the same or different from native or unmodified enzymes. The present invention contemplates methods and compositions comprising whole enzymes, fragments, peptides, binding regions, active sites or other functional regions, segments, sequences and promoter and control sequences of oxalate reducing enzymes.

The present invention comprises use of recombinant proteins, and recombinant proteins mutated so as to cause the proteins to be insoluble or only slightly soluble in the cytoplasm of the host at rates higher than those seen in wild-type or not-mutated recombinant proteins. Additionally, these recombinant proteins are not found as inclusion bodies in the host cell. There are several methods to modify protein solubility such as replacement of hydrophilic residue(s) with less hydrophilic residue(s), replacement of charged amino acid(s) with non-charged amino acid(s), and/or addition of hydrophobic peptide tail(s) at the C- and/or N-terminus. The modifications should not inactivate the protein and the modified protein with low solubility should be expressed in an active form by the host cell, such as by *E. coli*. The present invention comprises methods for mutation of oxalate reducting enzymes, and the mutant enzymes, including, but not limited to, oxalate decarboxylase, oxalate oxidase, oxalyl co-A decarboxylase and formyl CoA transferase. The mutations would preferably not decrease or inactivate the functionality of the enzyme.

An example of mutations contemplated by the present invention is described. Both the N- and C-terminals of OxDC are distant from the catalytic sites and are quite flexible. The flexibility of the two termini as determined from x-ray crystallography reveal that the first 7 amino acids of the N-terminal tail and the last 6 amino acids of the C-terminus did not diffract due to conformational heterogeniety. Among the 6 residues at the C-terminus, C383 was chosen for mutation because there are many amino acids more hydrophobic or hydrophilic than Cys which can be selected to replace it. C383 represents the cysteine at position 383 in the oxalate decarboxylase amino acid sequence. In addition, C383 is the only Cys in OxDC, but has been shown to readily form disulfide bonds among OxDC hexamers and further generate aggregates. Replacement of C383 may eliminate formation of such aggregates and thus increase OxDC stability in solution. Mutations were introduced in the C-terminus region.

Multiple genes were created from the original yvrk gene sequence (the wild-type yvrk), oxalate decarboxylase. The original gene was from *Bacillus subtilis*, and the gene sequence was optimized for expression in *E. coli* using an algorithm from GenScript Corporation, Piscataway, N.J. The gene was optimized for codon usage, balancing GC content, removing repetitive elements, and ensuring the absence of internal restriction sites for cloning. The codon optimized gene resulted in a protein with the identical amino acid sequence as the wild-type yvrk.

Modifications were then made to the single cysteine codon of both the wild-type yvrk gene, and the optimized yvrk gene, resulting in additional unique gene sequences. The cysteine codon was replaced with a serine, arginine, or alanine codon.

The gene sequence of the wild-type yvrk gene may be optimized for additional expression systems such as *Pichia* or *Saccharomyces* using the same methods. In addition, expression in a *Bacillus* expression system may be improved by optimizing the gene for optimum codon usage and GC content, and removal of repetitive elements. Codon optimization may also be used for modification of the secondary structure of the protein at positions other than the cysteine codon already modified, or in addition to the cysteine modification, for example, as a method to improve pegylation, microsphere binding or encapsulation, as a method to improve pH stability at low pHs, or as a method to improve the activity of the protein.

Original yvrk sequence with the cysteine codon marked in bold.

SEQ ID 1
AAAAAACAAAATGACATTCCGCAGCCAATTAGAGGAGACAAAGGAGCAA
CGGTAAAAATC

CCGCGCAATATTGAAAGAGACCGGCAAAACCCTGATATGCTCGTTCCGC
CTGAAACCGAT

CATGGCACCGTCAGCAATATGAAGTTTTCATTCTCTGATACTCATAACC
GATTAGAAAAA

GGCGGATATGCCCGGGAAGTGACAGTACGTGAATTGCCGATTTCAGAAA
ACCTTGCATCC

GTAAATATGCGGCTGAAGCCAGGCGCGATTCGCGAGCTTCACTGGCATA
AAGAAGCTGAA

TGGGCTTATATGATTTACGGAAGTGCAAGAGTCACAATTGTAGATGAAA
AAGGGCGCAGC

TTTATTGACGATGTAGGTGAAGGAGACCTTTGGTACTTCCCGTCAGGCCT
GCCGCACTCC

ATCCAAGCGCTGGAGGAGGGAGCTGAGTTCCTGCTCGTGTTTGACGATGG
ATCATTCTCT

GAAAACAGCACGTTCCAGCTGACAGATTGGCTGGCCCACACTCCAAAGA
AGTCATTGCT

GCGAACTTCGGCGTGACAAAAGAAGAGATTTCCAATTTGCCTGGCAAAGA
AAAATATATA

TTTGAAAACCAACTTCCTGGCAGTTTAAAAGATGATATTGTGGAAGGGCC
GAATGGCGAA

GTGCCTTATCCATTTACTTACCGCCTTCTTGAACAAGAGCCGATCGAATC
TGAGGGAGGA

AAAGTATACATTGCAGATTCGACAAACTTCAAAGTGTCTAAAACCATCGC
ATCAGCGCTC

GTAACAGTAGAACCCGGCGCCATGAGAGAACTGCACTGGCACCCGAATAC
CCACGAATGG

CAATACTACATCTCCGGTAAAGCTAGAATGACCGTTTTTGCATCTGACGG
CCATGCCAGA

ACGTTTAATTACCAAGCCGGTGATGTCGGATATGTACCATTTGCAATGGG
TCATTACGTT

GAAAACATCGGGGATGAACCGCTTGTCTTTTTAGAAATCTTCAAAGACGA
CCATTATGCT

GATGTATCTTTAAACCAATGGCTTGCCATGCTTCCTGAAACATTTGTTCA
AGCGCACCTT

GACTTGGGCAAAGACTTTACTGATGTGCTTTCAAAAGAAAAGCACCCAGT
AGTGAAAAAG

AAATGCAGTAAA

Yvrk gene sequence optimized for *E. coli*, with restriction sites at the 5' and 3' ends (underlined), and the cysteine codon marked in bold.

SEQ ID 2
<u>CATATG</u>AAAAAACAGAATGACATTCCACAGCCGATTCGCGGCGATAAAG
GCGCGACCGTC

AAAATTCCTCGCAATATCGAACGCGACCGCCAGAATCCGGATATGCTGG
TGCCGCCGGAG

ACGGACCATGGCACGGTGTCTAACATGAAATTCTCTTTTAGCGATACCC
ACAACCGCCTG

GAAAAAGGTGGCTACGCGCGCGAGGTTACCGTCCGTGAACTGCCAATTA
GCGAAAATCTG

GCTTCGGTTAACATGCGTCTGAAACCAGGTGCTATCCGTGAGCTGCACT
GGCACAAGGAA

GCGGAATGGGCGTATATGATTTACGGTTCAGCACGTGTTACCATCGTAG
ACGAGAAAGGT

CGTAGCTTTATCGATGATGTTGGCGAAGGTGATCTGTGGTATTTCCCAT
CTGGCCTGCCG

CATTCGATTCAGGCGCTGGAAGAAGGCGCTGAATTTCTGCTGGTGTTCG
ATGATGGTTCC

TTTTCTGAAAACAGCACGTTCCAGCTGACGGATTGGCTGGCGCACACGC
CGAAAGAAGTC

ATTGCGGCCAATTTTGGGGTAACCAAAGAAGAAATTTCCAACCTGCCGG
GCAAAGAAAAG

TATATTTTTGAGAATCAGCTGCCGGGCTCTCTGAAGGACGATATTGTAG
AAGGCCCTAAC

GGTGAGGTGCCGTATCCGTTCACCTATCGTCTGCTGGAGCAGGAACCGA
TTGAAAGCGAA

GGCGGTAAAGTTTATATCGCAGATTCCACTAACTTTAAAGTCTCCAAGA
CCATTGCCAGC

GCCCTGGTCACCGTGGAACCGGGAGCGATGCGCGAGCTGCACTGGCATC
CGAACACGCAC

GAATGGCAGTATTATATTTCCGGCAAAGCACGCATGACCGTTTTTGCCT
CAGATGGACAC

GCTCGCACGTTTAATTATCAAGCGGGTGATGTTGGCTACGTTCCTTTCG
CCATGGGCCAT

TATGTAGAAAATATCGGCGATGAACCACTGGTGTTTCTGGAGATCTTTA
AAGATGACCAC

TATGCCGATGTTTCACTGAATCAGTGGCTGGCCATGCTGCCGGAAACTT
TTGTTCAGGCG

CATCTGGACCTGGGTAAAGACTTTACGGATGTGCTGAGCAAAGAAAAAC
ACCCGGTAGTCAAGAAGAAATGCAGTAAA<u>GGATCC</u>

Other sequences of the present invention comprise the yvrk gene of SEQ ID 1 comprising bases 1142-1152 of SEQ ID 3-16. NOs 3-8 are serine, NOs. 9-14 are arginine, and NOs 15-19 are alanine.

SEQ ID 3
ATCTAGTAAA

SEQ ID 4
ATCCAGTAAA

SEQ ID 5
ATCAAGTAAA

SEQ ID 6
ATCGAGTAAA

SEQ ID 7
AAGTAGTAAA

SEQ ID 8
AAGCAGTAAA

SEQ ID 9
ACGTAGTAAA

```
                        SEQ ID 10
ACGCAGTAAA

SEQ ID 11
ACGAAGTAAA

SEQ ID 12
ACGGAGTAAA

SEQ ID 13
AAGAAGTAAA

SEQ ID 14
AAGGAGTAAA

SEQ ID 15
AGCTAGTAAA

SEQ ID 16
AGCCAGTAAA

SEQ ID 17
AGCAAGTAAA

SEQ ID 18
AGCGAGTAAA

SEQ ID 19
AGGAAGTAAA
```

Particles Including Spray-Dried Particles

An aspect the present invention relates to particles comprising oxalate reducing enzymes and a polymeric material. The oxalate reducing enzyme may be a mutant recombinant oxalate reducing enzyme protein.

The particles should be able to degrade oxalate in the stomach of a human or animal, i.e. formation of the particles may not lead to marked loss of activity of the enzymatic activity and the properties of the particles must be to protect the enzymes contained in the particles from degradation and/or inactivation. Thus, the enzyme must be active at a pH corresponding to the pH normally found in the stomach (pH 2.5-5 after meal) or, alternatively, a pH-regulating agent may be incorporated in the particles as well or admixed with the particles before administration. Suitable pH-regulating agents include buffer substances such as those well known to the skilled person.

Particle formation (in combination with the use of a specific method for preparing the particles and specific polymers or copolymers employed) is contemplated to protect the enzyme protein from pepsin digestion to ensure activity of enzyme. Particle formation of proteins and polymeric material is contemplated by the present invention. As used herein, particle formation means the association of protein with a polymeric or copolymeric solution to form small particles comprising active enzymes and polymers or co-polymers. Such methods of formation of active enzyme particles increase the amount of active enzyme in the particle and may increase the efficacy of a dosage form containing the particles when used in a treatment or prevention regimen. The particle formation aids in the protection of the enzyme from pepsin digestion.

It is important to ensure that the method employed for particle formation does not involve reagents, solvents, temperatures, apparatus etc. that leads to a risk for inactivation of the enzymes. Thus, care should be taken to avoid methods involving e.g. organic solvents, high temperatures and low or high pH.

There are many approaches to particle formation such as coacervation, phase separation, polymerization, spray-drying, electrostatic methods, and air suspension approaches.

Spray drying is a mechanical micro-encapsulation method developed in the 1930s. This technique utilizes a drug or active substance, mixed with polymer(s) and/or other excipients to form the feed, which can be either a solution, suspension, dispersion, or emulsion. The feed is atomized into droplets and introduced in the drying chamber along with dry hot gas. Droplets lose moisture to the dry hot gas and form dry powders.

A suitable method for making active enzyme particles of the present invention is spray-drying. In such a method the enzyme(s) and polymer(s) are dispersed or dissolved in an aqueous medium and via a nozzle loaded into a suitable spray-drying apparatus. The conditions are mild, even if a relatively high inlet and outlet temperatures are employed, the examples herein show that the activity of the enzyme(s) contained in the particles remain at a high level, and even higher levels have been observed. Other methods may also be of relevance provided that the activity of the enzyme(s) is not seriously destroyed (at least 80% of the activity should be maintained). With respect to spray-drying, the examples herein show a remaining activity of at least 85% and remaining activities of at least 90% and at least 100% are also seen.

In many particle formation methods, the protein is usually provided in a solution. Normally, the proteins in a particle are distributed homogenously, which leads to difficulties in achieving an effective concentration of the enzyme inside the particles to provide an adequate or increased level of enzyme activity. In a spray-drying method the protein may be provided in solution or in dispersion or suspension, where the enzyme protein is in a solid state, for example, as an enzyme protein nano- or micro-agglomeration. When the particles are provided to the intended delivery site, the solid enzyme nano- or micro-agglomeration in the particles is solvated and forms an effective concentration of an enzyme solution. The enzyme concentration may be at a level such that the specifc activity increases For example, the C383S mutant of OxDC only minimally dissolves in buffers between pH 4.5-7.8, and it can be prepared as a protein nano- or micro-agglomeration in a water suspension at pH 4.5-7.8. The C383S nano- or micro-agglomeration suspension then is mixed with a polymer solution or suspension, and particles are formed by spray drying or other drying technologies. The concentration of the C383S mutant OxDC in the particles shows a specific activity of the C383S mutant of up to 141% of its original specific activity. Thus, spray-drying is the preferred method for making the particles.

In the non-limiting examples herein are described methods of how to combine the enzyme in a polymeric material. A person skilled in the art may find other methods suitable for use in order to prepare a composition according to the present invention. By incorporation of the enzyme in a polymeric material, the enzyme obtains a certain protection against conditions similar to gastric fluid with respect to pH and pepsin. The resulting oxalate reducing enzyme composition appears as particles, i.e. discrete units in micron- or nano-size.

Normally, the particles of a composition of the invention have an average diameter of from about 50 nm to about 1 mm, such as, e.g., from about 500 nm to about 500 µm, from about 1 µm to about 500 µm, from about 2 µm to about 100 µm, from about 4 µm to about 80 µm, from about 6 µm to about 60 µm, from about 8 µm to about 40 µm, from about 10 µm to about 20 µm.

Many different polymers and copolymers may be suitable for particle formation such as natural or synthetic polymers including but not limited to, alginate, dextran, cellulose, collagen, chitosan, alginate, pectin, hyaluronic acid, PLGA, polyvinyl alcohol (PVA), poly(acrylic acid), poly(lactic acid), poly(ethylene glycol), poly(esters), etc.

However, in the present context Eudragit® polymers have been found to lead to the desired result, i.e. maintaining a suitable activity of the enzyme and sufficient protection of the enzyme from pepsin or other enzymes present in the stomach as well as the low pH of the content of the stomach.

Eudragit® polymers are polymers based on poly(meth) acrylates and are available in a number of varieties e.g. for gastoresistance and GI targeting, for moisture protection and odor/taste masking, for time-controlled drug release. Some Eudragit® polymers (Eudragit® series L, S and FS) have different solubility in acidic and neutral/alkaline environment and pH-cut off (i.e. the value at which the polymer becomes soluble) varies from 5.5 to >7. Other Eudragit® polymers (series E and EPO) are soluble in gastric fluid up to pH 5 and swellable at higher pH values. Some Eudragit® polymers (series RL, RS, NE and NM) are insoluble and have a pH independent swelling.

As seen from the examples herein, Eudragit® polymers of the first and third group mentioned above are suitable for use in the particles of the present invention. In the first group that includes Eudragit® L100-55, L30-55, L100, L12.5, S100, S12.5, and FS30D the polymer is a methacrylic copolymers with a carboxylic acid as a functional group, i.e. the polymer is an anionic polymer. In the second group that includes Eudragit® E100, E12.5 and EPO, the polymer is aminoalkyl methacrylate copolymers with dimethyl aminoethyl as a functional group. In the last group that includes Eudragit® RL30, RL PO, RL100, RL12.5, RS30D, RS PO, RS100, RS12.5, NE 30D, NE40D, NM30D, the polymer is aminoalkyl methacrylate copolymers with trimethyl-ammonioethyl-methacrylates as a functional group (series RL and RS) or the polymer is neutral polymers of methacrylates (series NE and NM). The polymers are available from Evonik Industries.

The concentration of the polymer in the particles is from about 5 to about 80% w/w such as from about 5 to about 70% w/w, from about 5 to about 60% w/w, from about 5 to about 50% w/w, from about 10 to about 50% w/w or from about 10 to about 40% w/w.

In the examples herein, suitable particles have been formed using Eudragit® L-100, L-100-55, RS, RL, i.e. representing group one and three above.

The composition that is spray-dried may apart from the enzyme and the polymeric material also contain one or more excipients or additives. Excipients can be any molecules that protect the enzyme from heat, dehydration and storage such as sugars, amino acids, surfactants, salt, etc. Pharmaceutically acceptable excipients like those described herein may also be employed.

The particles may be formed by known methods, preferably by spray-drying. After forming the particles comprising one or more enzymes and a polymeric material, the particles may be further treated, such as by drying, freeze-drying or lyophilization. Although freeze-drying does not generate particle formation, it can dry already formed particles comprising enzymes and polymeric material. The particles can be in a state of suspension, dispersion, or emulsion, which are then subjected to freeze dry conditions. Freeze-drying avoids heating the enzymes and makes the drying process suitable for heat sensitive proteins. Freeze-drying or other methods (e.g. coating) may be omitted and then particles of polymer and oxalate reducing enzymes are formed solely by spray drying. Such particles may then be formulated into oral pharmaceutical or food formulations such as by mixing with bulking agent and e.g. filling in sachets, adding the particles to capsules, compressing the particles into tablets, incorporating the particles in chewable tablets, incorporating the particles into quick dissolve or oral dissolve tablets, or adding particles to liquids, syrups, elixirs or foodstuffs.

For example, particles were made by combining oxalate decarboxylase (OxDC) with a polymeric material, Eudragit L100. For comparison, OxDC was lyophilized with arginine buffer only. Both the lyophilized enzyme, without polymeric material and the particles formed by spray-drying the combination of OxDC with Eudragit L100, followed by freeze-drying, resulted in 100% recovery yields and no loss of activity. The particles comprising OxDC with Eudragit L100 were protected from pepsin degradation in solutions from pH 3.25 to pH 5.0 for at least 40 minutes, for at least 60 minutes, for at least 90 minutes, for at least 120 minutes.

The present invention comprises particles of oxalate reducing enzymes, wild-type or mutated, and a polymeric material which protects the enzymes from degradation under gastric conditions (pepsin). It can be envisaged that the particles may comprise any oxalate reducing enzymes or cofactors, and the present invention contemplates compositions that comprise oxalate reducing enzymes, such as, oxalate decarboxylase, oxalate oxidase, oxalyl-CoA decarboxylase or formyl CoA transferase; or a combination of oxalyl-CoA decarboxylase and formyl CoA transferase, or a combination of any of these, and such enzymes may be native or wild-type enzymes or may be non-native or mutated enzymes having mutations, modifications or alterations in nucleic acid sequence, amino acid sequence, binding groups, carbohydrates, or lipids. These enzymes use oxalate as a substrate or are active in a step in oxalate metabolism or catabolism.

Thus, the particles of the invention protect the oxalate-degrading enzyme from the gastrointestinal environment. Furthermore, the particles of the invention do not substantially release the enzyme to the gastrointestinal environment. In other words, the enzyme remains in the particle after oral administration for a sufficient period of time to enable oxalate in the stomach to be degraded or reduced. The enzymes may be released from the particles while in the stomach or after leaving the stomach, depending on the type of polymer used to make the particle or on treatments to the particle, such as coating or cross-linking. In the particles the polymeric material may function as a protective carrier for the enzyme and at the same time may allow the substrate, i.e. oxalate, to diffuse or otherwise be transported into the composition to enable an in situ degradation of oxalate. A feature of the particles of the present invention is their ability to retain the enzymatic activity for a period of time longer than that observed for an enzyme that is not in the form of such particles, especially in the presence of pepsin. Accordingly, one aspect the present invention relates to particles comprising one or more oxalate reducing enzymes and a polymeric material, wherein the enzyme retains at least two times the activity of the one or more free enzymes (i.e. not in the form of such particles), obtained from the same batch, upon incubation a buffer containing 3.2 mg/ml pepsin at pH 3.25 at 37° C. for at least 60 minutes. It is important that the test conditions for the particles according to the invention and the free enzymes are the same, for example, with respect to the nature and purity of the enzyme, the initial concentration of the enzyme, the test volume, the composition of the incubation medium (e.g. the buffer), the temperature, etc.

Normally, the enzyme contained in the particles retains at least three times the activity, at least four times the activity, or at least five times the activity of the one or more free enzymes obtained from the same batch upon incubation in a buffer containing 3.2 mg/ml pepsin at pH 3.25 at 37° C. for at least 30 minutes, at least 45 min, at least 60 minutes, at least 75 minutes, at least 90 minutes, at least 105 minutes or at least 120 minutes.

In a specific embodiment, the one or more oxalate reducing enzymes in the particles of the invention retain at least two times, at least 10 times, at least 50 times or at least 100 times, the activity of the one or more free enzyme, obtained from the same batch, upon incubation in a buffer containing 3.2 mg/ml pepsin at pH 3.25 at 37° C. for at least 60 minutes.

Suitable buffer substances for providing a buffer solution having a specific pH are known to persons skilled in the art. Examples are glycine buffers, acetate buffers, phosphate buffers, borate buffers and the like. The buffer solution may contain additional ingredients such as e.g. inorganic salt in order to adjust the ionic strength of the buffer solution, or one or more proteases like e.g. pepsin in order to ensure that the conditions in the buffer solutions challenge whether the embedded enzyme can withstand such harsh conditions.

Other polymers may also be present in the particles together with one or more poly(meth)acrylate polymer. Such polymers include, but are not limited to, man-made or natural polymers, including, but not limited to, i) a polysaccharide: alginate including alginic acid, alginate e.g. sodium alginate, potassium alginate, ammonium alginate, calcium alginate, propane-1,2-diol alginate, acacia, carrageenan, chitosan and its derivatives, chondroitin sulfate, dextran derivatives, heparin, hyaluronic acid, inulin, a cellulose or a cellulose derivative including methylcellulose, carboxymethylcellulose, sodium carboxymethylcellulose, hydroxypropylcellulose, hydroxypropylmethylcellulose, ethylmethylcellulose, or the like or combinations thereof; ii) a mucopolysaccharide, iii) a gum including locust bean gum, guar gum, tragacanth, agar, acacia gum, xanthan gum, karaya gum, tars gum, gellan gum, or the like or combinations thereof; iv) a gelling- or swelling agent including hydrocolloids and hydrogelling agents such as, agar, carrageenan, gelatin, polyvinylpyrrolidone, or the like, or combinations thereof; v) others like e.g. protein and polyamide: collagen, albumin, protamine, spermine, synthetic polymer: poly (acrylic acid), polyphosphoric acid, tripolyphosphate, poly (L-lactic acid), poly (vinyl alcohol), poly (DL-lactic acid-co-glycolic acid), Eudragit polymers, including but not limited to L-100, L-100-55, RS, RL, or copolymers or mixtures and combinations thereof. In an embodiment, the polymeric material is Eudragit polymers, including but not limited to L-100, L-100-55, RS or RL.

Other polymeric materials that may be added to the poly (meth)acrylate polymer formulation may be biopolymers or synthetic polymers. Examples of biopolymers include, but are not limited to, proteins, polysaccharides, mucopolysaccharides, heparin, heparin sulfate, heparinoids, dermatan sulfate, pentosan polysulfate, chondroitin sulfate, cellulose, agarose, chitin, carrageenin, linoleic acid, and allantoin, cross-linked collagen, fibronectin, laminin, elastin, cross-linked elastin, collagen, gelatin, hyaluronic acid, chitosan alginate, dextran, methylcellulose, polylysine, and natural rubber. In the compositions of the present invention wherein polymeric matrices are formed, these matrices are porous such that small water soluble molecules can enter and exit the polymeric matrix, including, but not limited to molecules such as oxalate, formic acid, formate, carbon dioxide, oxygen, or oxalyl-CoA. A concentration of the polymeric material in a composition of the invention is normally in a range from 10% to 90% of the total dry materials In addition to the one or more enzymes and a polymeric material, the particles may also contain one or more additives such as, e.g., pH adjusting agents, buffering agents, solubilizing agents, stabilizers, preservatives, cofactors for the enzymes or one or more pharmaceutically acceptable excipients such as, e.g. fillers, bulking agents, diluents, carriers or the like.

Moreover, it may be advantageous to create a localized acidic pH environment around a protein when the physiological conditions result in a pH well below the reasonable working range of the enzyme. For example, in a lower pH location, an oxalate reducing protein with maximum activity at pH 4 would benefit from a delivery vehicle capable of increasing the local pH in the proximity around the enzyme to around pH 4.

In addition, it may be desirable to include a buffer in the delivery vehicle in the form of a base, base containing or base generating material that works in conjunction with the in vivo pH, or the localized pH, or a combination of both to optimize/control the local pH around the enzyme. These buffers may include salts of organic or inorganic compounds or a number of other buffers. It is understood that the pKa of the conjugate acids of which the buffering materials are associated/derived from can be utilized in the appropriate selection of buffering materials.

In some case a polymeric material may be applied to the particles (e.g. as a coating) in order to increase the shelf stability of the particles or to inhibit a degradation of the enzyme. Such polymeric material may, if relevant, moreover be cross-linked. The cross-linking may be by physical or chemical cross-linking. Physical cross-linking may comprise opposite charged polymers cross-linked with each other by salt bonds (for example: chitosan, which is positively charged, cross-links with tripolyphosphate or heparin, which are negatively charged polymers), charged polymers cross-link with opposite charged ions (for example: alginate with $Ca^{2+}$, carboxymethyl-cellulose with $Al^{3+}$). The term "physical cross-linking" used in the present context also includes non-covalent bindings and/or interactions.

Chemical cross-linking generally comprises cross linking by cross-linkers with two reactive functional groups such as by polymer bearing amine groups such as proteins, polyamide, chitosan and its derivatives, may be cross-linked through glutaraldehyde or genipin. UV irradiation can be used to induce polymers bearing light sensitive groups to form covalent cross-links.

The properties of the particles, for examples: micro-environmental buffer capacity, mechanical strength, particle size, oxalate diffusion rate, interactions with enzymes, largely depend on selected polymer(s), polymer composition and ratio, optional cross-linking methods and preparation procedures.

The particles may also be provided with a coating. Such a coating has generally the same function as the polymeric material, i.e. to avoid a substantial decrease in the enzymatic activity of the enzyme embedded in the polymer during storage and/or after oral administration.

Suitable coating materials are such materials that allow an aqueous composition containing oxalate to diffuse into, or otherwise enter, the particle of the invention. As mentioned above, the substrate (i.e. the oxalate-containing medium) enters into the particle composition of the invention so that enzymatic degradation of oxalate can occur. Accordingly, coating materials resulting in either diffusion coating or otherwise permeable coatings (e.g. coatings containing pore-forming substances that are substantially water-soluble) can be applied.

Examples of suitable coating materials include, but are not limited to, the materials contemplated as the polymeric materials. A coating material may be chosen that is different than that used as the polymeric material, but the polymeric material and the coating material may also be the same. Specific examples of coating materials are film-forming agents such as, e.g. polyvinylpyrrolidone, hydroxypropylmethylcellulose (HPMC), hydroxyethylcellulose, hydroxypropylcellulose, polydextrose, maltodextrin, or other polysaccharides including chitosan, alginates and hyaluronic acid. If present, the coating material is normally applied in such an amount the weight gain of the particles is at the most about 40%.

Compositions

In order to deliver the particles as described above to the stomach of a human or an animal, the particles may be formulated into a suitable dosage form for oral administration.

Oral formulations include, but are not limited to, capsules, tablets, chewable tablets, quick dissolve tablets, oral dissolve tablets, liquids, and other known oral formulations suitable for pharmaceutical or food use.

A composition of the invention is suitable for use for oral administration to a subject. A composition is provided as oral pharmaceutical formulations, which may be delivered to the oral cavity, the mouth, a buccal patch, to the stomach, attached to the stomach mucosa, in a slow release liquid, in a quick release tablet in the mouth or stomach, coating the esophagus, in a liquid or solid form accompanying food, prior to ingesting food, or immediately after ingesting food.

Compositions of the present invention reduce dietary oxalate under gastric conditions, such as those found after consumption of food, such as in the presence of proteases. Compositions of the present invention reduce oxalate in the stomach of humans and other animals. Compositions reduce oxalate, e.g. oxalate in the gastrointestinal tract, notably in the stomach, and prevent at least a portion of exogenous oxalate (e.g. from food) from entering the systemic circulation.

A composition of the present invention comprises particles as described above. The particles comprises one or more oxalate reducing enzymes and a polymeric material; or particles comprising other enzymes, cofactors and co-enzymes related to oxalate degradation pathways combined with a polymeric material, or both particles, provided separately or together in an oral dose form.

Such compositions comprising particles comprising other enzymes, co-factors, or co-enzymes alone may be administered simultaneously with, sequentially with, or before or after, administration of compositions of particles comprising oxalate reducing enzymes. The compositions comprising particles comprising other enzymes, co-factors, or co-enzymes alone may be combined with compositions comprising particles comprising oxalate reducing enzymes to form a single administrative dose to provide an effective amount of oxalate reduction in the gastric tract.

Compositions may comprise oxalate reducing enzymes that are recombinant proteins that have a native sequence, i.e., having the gene and protein sequence of oxalate reducing enzymes as found in nature, or may be recombinant proteins that are non-native, mutated oxalate reducing enzymes that have nucleic acid or protein mutations or are altered in some manner. For example, a non-native oxalate reducing enzyme, such as oxalate decarboxylase, may have one or more amino acid replacements. The enzymes are described in detail herein.

A composition of the present invention comprises particles comprising mutated recombinant oxalate reducing enzyme proteins and a polymeric material wherein the specific activity of the mutated recombinant oxalate reducing enzyme is higher in the particle than the specific activity of the protein free in solution. Such particles may be administered in compositions such as oral formulations e.g. pharmaceutical or food formulations.

Formulations include, but are not limited to, sachets, tablets, capsules, quick dissolve tablets, oral dissolving tablets, chewable tablets, powders, granules, pellets, liquids, syrups, elixirs, or other oral dosage formulations known to those skilled in the pharmaceutical art. The oral formulations optionally may comprise buffering capabilities. For example, a composition may comprise buffering compounds that adjust the pH of the composition and thus the surrounding environment, such as the stomach once the composition is ingested, to about pH 4. With the environment of the enzyme at pH 4, the enzymes of the present invention are active and reduce oxalate. Such buffer compounds may be acetate, citrate, phosphate or other buffer compounds. A feature of a composition of the present invention is the ability of the particle to protect the oxalate-degrading enzymes from degradation by conditions such as those found in the gastric environment including, but not limited to, degradation by a protease such as pepsin.

The compositions of the present invention may also comprise one or more additional factors which may improve the enzyme activity. These additional factors may be, e.g., oxalyl CoA, $MgCl_2$, and/or thiamine diphosphate (an active form of vitamin $B_1$), or pH buffering compounds.

The composition administered is normally in solid form e.g. in the form of powders or in a solid dosage form e.g. in the form of sachets, capsules or tablets (e.g. the particles are further processed into a suitable dosage form by methods well-known by a person skilled in the art). To this end, suitable pharmaceutically acceptable excipients may be added such as, e.g., fillers, binders, disintegrants, colors, flavors, pH-adjusting agents, stabilizers etc. Moreover, one or more further therapeutically and/or prophylactically substances may be added and/or other enzymes, cofactors, substrates, coenzymes, minerals and other agents that are helpful in the reduction of oxalate.

Examples of suitable pharmaceutically acceptable excipients include: dextrins, maltodextrins, dextrose, fructose, glucose, lactose, cellulose derivatives including carboxymethylcellulose calcium, carboxymethylcellulose sodium, hydroxypropylcellulose, hydroxypropylmethylcellulose (HPMC), microcrystalline cellulose (e.g., various grades of Avicel®), starches or modified starches (e.g. potato starch, maize starch, rice starch, pre-gelatinised starch), polyvinyl acetate, polyvinylpyrrolidone, agar, sodium alginate, sodium croscarmellose, calcium hydrogen phosphate, calcium phosphate (e.g. basic calcium phosphate, calcium hydrogen phosphate), calcium sulphate, carboxyalkylcellulose, dextrates, dibasic calcium phosphate, gelatine, gummi arabicum, hydroxypropyl cellulose, hydroxypropylmethylcellulose, methylcellulose, polyethylene glycol, polyethylene oxide, and as lubricants: talc, magnesium stearate, calcium stearate, stearic acid, hydrogenated vegetable oils and the like.

The compositions of the present invention are suitable for use reducing oxalate levels in humans or animals. They may also be suitable for treating or preventing oxalate-related conditions including, but not limited to, hyperoxaluria, absorptive hyperoxaluria, enteric hyperoxaluria, primary hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and patients who have undergone gastrointestinal surgery and bariatric surgery (surgery for obesity), and/or who have undergone antibiotic treatment. The present invention contemplates the treatment and prevention of oxalate-related conditions in humans and animals.

An oxalate-degrading particle or composition of the invention is administered in a desired amount, such as an amount that is sufficient to degrade substantially all oxalate normally present in a standard meal. Depending on the food choices, an average Western diet can contain 100 to 300 mg of oxalate/day. In general, about 0.2 g of the particles comprising an oxalate reducing enzyme (equal to 50 mg of OxDc in 1 mL of suspension of particles) can degrade about 300 mg oxalate in less than 30 min in simulated gastric conditions. Typical simulated gastric conditions were generated as: 100 ml of USP simulated gastric juice mixing with 400 grams of balanced western style meal (broken into small pieces) and 500 grams of water, yielding pH in the range of 3.5-4.5. Reduction of oxalate absorption may be shown by a reduction in oxalate levels found in the blood, serum or urine, or other body fluids.

An effective amount comprises an amount of activity units of oxalate-reducing enzyme activity that will reduce a portion of the oxalate present, or a level of activity units of oxalate-reducing enzyme activity that will initiate a reduction in the amount of oxalate or maintain a lowered amount of oxalate in the individual, compared to the amount of oxalate present before administration of the composition. The number of activity units of oxalate-reducing enzyme activity that can be used in a single dose composition normally ranges from about 0.001 units to about 20,000 units, from 0.01 to 15,000 units, from 0.1 to 10,000 units, from 1 to 5000 units, from 10 to 4000 units, from 50 to 3,000 units or from 100 to 2,500 units. In those cases where low doses are required the range may be from about 5 units to 100 units, from 0.05 to 50 units, to 0.5 to 500, from about 0.01 units to about 50 units, from about 0.01 units to about 5 units, from about 1 units to about 100 units, from about 25 units to about 50 units, from about 30 units to about 100 units, from about 40 units to about 120 units, from about 60 units to about 15 from about 50 units to about 100 units, from about 100 units to about 500 units, from about 100 units to about 300 units, from about 100 units to about 400 units, from about 100 units to about 5,000 units, from about 1,000 units to about 5,000 units, from about 2,500 units to about 5,000 units, from about 0.001 units to about 2,000 units and all ranges encompassed therein. A unit of the enzyme is the amount of enzyme that will degrade one micromole of oxalate per minute at 37° C.

Use of Particles and Compositions—Method for Treatment

Methods of the present invention comprise providing particles, preferably spray-dried particles, compositions to the stomach of a human or animal, for example, providing a composition that enables reducing oxalate in the stomach to reduce the absorption of oxalate from the gastrointestinal tract. The composition of particles may protect the oxalate-reducing enzymes from the enzyme-damaging environment in the stomach, and allow the enzymes to maintain enzymatic activity in such a harsh environment.

Methods of treatment and prevention comprise providing compositions taught herein in which oxalate reducing enzymes are contained in particles together with a polymeric material.

The particles and compositions of the present invention are suitable in methods of reducing oxalate absorption in the body and are used in the treatment or prevention of oxalate-related conditions including, but not limited to, hyperoxaluria, absorptive hyperoxaluria, enteric hyperoxaluria, primary hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and patients who have undergone gastrointestinal surgery and bariatric surgery (surgery for obesity), and/or who have undergone antibiotic treatment.

Methods of the present invention comprise administering a composition that enables reducing oxalate in the stomach in order to avoid absorption of oxalate by the body of a human or animal, for example, by reducing oxalate from food sources. A method of providing oxalate reducing enzymes to the stomach is to provide oxalate reducing enzymes in a polymeric material in an oral pharmaceutical formulation.

A reduction in oxalate absorption may be achieved by providing oxalate-degrading enzymes to the gastrointestinal tract, particularly the stomach, thus lowering the concentration of available oxalate for absorption. Reduction of oxalate in the stomach will also reduce the amount of oxalate going into the intestine for absorption in this segment of the gastrointestinal tract. In addition to absorptive pathways, oxalate secretory pathways have been recently identified in the human stomach. The compositions of the present invention would also be useful in degrading the oxalate secreted into the stomach from the circulatory system, and thus the methods of the present invention contemplate an overall reduction of the oxalate load in an individual.

Methods for reducing oxalate in a human or animal comprise administering an effective amount of a composition comprising one or more oxalate-reducing enzymes or fragments having oxalate reducing activity in the particle compositions of the present invention to a subject, human or animal, and reducing oxalate present. The reduction may be measured in any tissue or body fluid environment of the subject. Body fluids include secretions of the body such as nasal or gastric secretions, saliva, blood, serum, urine, chyme or digestive matter, tissue fluid, and other fluid or semi-solid materials made by humans or animals. For example, oxalate reducing enzyme particle compositions can be administered orally to a human or animal and the oxalate-reducing enzyme activity reduces the oxalate present in the stomach of the human or animal. Particle compositions of the present invention may be mixed in liquids, food or other dietary materials and provided to a human or animal so that the oxalate-reducing enzyme activity of the particles is effective in the stomach environment. Particle compositions of the present invention may also be mixed with foodstuffs or other materials in which oxalate is found and the oxalate-reducing enzyme activity of the particles reduces the oxalate present in the foodstuff or other materials.

Methods for reducing absorption of oxalate by a human or animal and treating and preventing oxalate-related conditions comprise administering a composition comprising particles comprising an effective amount of oxalate-reducing enzymes. An effective amount comprises an amount of activity units of oxalate-reducing enzyme activity that will reduce a portion of the oxalate present, or a level of activity units of oxalate-reducing enzyme activity that will initiate a reduction in the amount of oxalate present in a meal or present in the tissues or bodily fluids of the subject or maintain a lowered amount of oxalate in the subject compared to the amount of oxalate present before administration of the composition.

In a treatment method, an effective amount of a particle composition as taught herein is administered orally to be ingested by a subject at least once a day, at least twice a day, at least three times a day, at least four times a day or more if necessary, and such administration can be for one day, two days, three days, four days, five days, or a week, two weeks, three weeks, or a month, two months, three months, four months, five months, six months, more than six months, one year, two years, or for years or continuously through the life of the patient. Such treatment may be continued to maintain the desired oxalate levels in a subject.

All patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention are provided herein, the present invention is not limited to these embodiments. There are numerous modifications or alterations that may suggest themselves to those skilled in the art.

The present invention is further illustrated by way of the examples contained herein, which are provided for clarity of understanding. The exemplary embodiments should not to be construed in any way as imposing limitations upon the scope thereof. On the contrary, it is to be clearly understood that changes can be made to various other embodiments, modifications, and equivalents thereof which, after reading the description herein, may suggest themselves to those skilled in the art without departing from the spirit of the present invention and/or the scope of the appended claims.

EXAMPLES

Methods

Assay for Enzymatic Activity

Oxalate decarboxylase activity is quantified by determining the rate of formate formation. An activity mixture (390 μl) containing 40 mM oxalate in 40 mM citric acid, pH 4.0, is incubated at 37° C. for 5 min and the reaction is initiated by the addition of 10 μl of an OxDC solution containing 0.2-1 mg/ml of OxDC. After 10 minutes of reaction time, 100 μl of 0.5 M H2SO4 is added to quench the reaction. After centrifugation at 14000 g for 10 min, the supernatant is analyzed by HPLC.

All HPLC analyses are performed using an Agilent 1100 Series system. Separations are at 40° C. on an Aminex HPX-87H (Bio-Rad) strong ion exchange column (300×7.8 mm ID), protected with an Aminex Cation H Micro-Guard cartridge (Bio-Rad) placed outside the heater. The mobile phase for all analyses is 5 mM H2SO4 (reagent grade (Sigma)) with a flow rate of 0.6 ml/min. Injection volume is 40 μl. Detection is at 210 nm and quantification is by formate peak area.

One unit of activity is defined as the amount of OxDC that produces one micromole of formate from oxalate in one minute under the above conditions, or a unit of the enzyme is the amount of enzyme that will degrade one micromole of oxalate per minute at 3TC.

Stability Test

After incubation of OxDc free enzyme or the composition in question containing the OxDc enzyme embedded in a polymeric material in 100 mM glycine buffer at pH 3.25 containing 3.2 mg/ml of pepsin for a certain period, the remaining OxDc activity was analyzed.

Example 1

A Process for Production of Oxalate Decarboxylase from *Bacillus subtilis* by *E. coli*

Cloning of YvrK Gene and Optimization of Gene Codons for Higher Expression

OxDC from *Bacillus subtilis* is a homohexameric enzyme. Each monomer contains 385 amino acids, with a molecular weight of approximately 44 kDa. The OxDC gene, known as YvrK, was PCR-amplified from *B. subtilis* genomic DNA and inserted into the pET9a plasmid (Novagen, catalog #69431-3) by way of NdeI and BamHI restriction sites.

The YvrK gene was codon optimized by Genscript Corp (Boston, Mass.). Some codons in the original gene sequence were changed to *E. coli* preferred codons in order to increase protein expression. The *E. coil* optimized gene was inserted back into a pET-9a vector through NdeI and BamHI restriction sites to generate pET-9a:YvrK and the sequence of the *E. coli* codon optimized gene was confirmed by DNA sequencing. The plasmid with the condon optimized gene was then transformed into *E. coli*. BL21(DE3) for OxDC production by induction with Isopropyl β-D-1-thiogalactopyranoside (IPTG).

Expression of Oxalate Decarboxylase (OxDC) in *E. coli* (Fermentation)

Expression of OxDC in *E. coli* BL21(DE3) was conducted at 3 different scales of fermentation: 0.4, 50 and 1000 L (liters) of media. In general, the fermentation process was initiated by inoculating the culture media with a seed culture (0.1% inoculum) of bacteria at 37° C. with shaking or agitation. IPTG was added to the culture to induce OxDC expression when $OD_{600}$=1.0-2.0. After induction, *E. coli* cells were harvested by centrifugation (less than 1000 L scale) or filtration using hollow fiber filters approximately 8-10 hours after induction (1000 L).

Purification of Oxalate Decarboxylase (OxDC) from *E. coli* Cells

Lysis of *E. coli* cells and collecting insoluble cell debris containing OxDC. The collected *E. coli* cells were lysed by homogenization, and the cell debris containing OxDC was collected by centrifugation. The cell debris pellet was first suspended in deionized (DI) $H_2O$ with a weight ratio of $H_2O$ to pellet of 3:1 to remove any remaining water soluble proteins and other *E. coli* cell components. The washed cell debris was collected again by centrifugation. Approximately 10 grams of cell debris pellet was obtained from 1.0 L of culture, which contained 40-200 mg of OxDC.

Extraction of OxDC by high concentration of $(NH_4)_2SO_4$. The washed cell debris was re-suspended in 3 times by weight of 50 mM Tris HCl buffer, pH 8.0 containing 0.75M $(NH_4)_2SO_4$ for extraction of OxDC. The suspension was stirred at 20-25° C. for 30 minutes and the extracted OxDC was collected by centrifugation. Approximately 60% of the expressed OxDC was usually extracted from the pellet by this method.

Anion exchange chromatography column. The extract was diluted 3 times with 50 mM Tris HCl, pH 8.0 and then passed through a Q-sepharose column which was pre-equilibrated with 50 mM Tris HCl, pH 8.0 containing 0.25 M $(NH_4)_2SO_4$. DNA and other impurities bound to the column while OxDC passes through and collected.

Hydrophobic interaction chromatography column with a gradient evolution. The $(NH_4)_2SO_4$ concentration in the OxDC solution collected from the Q-sepharose column was adjusted to 2.0 M by addition of solid $(NH_4)_2SO_4$ and was loaded into a pre-equilibrated phenyl-sepharose column. OxDC was eluted by way of an $(NH_4)_2SO_4$ gradient. OxDC was eluted into two main peaks at 1.3 M and 0.9 M $(NH_4)_2SO_4$ respectively (FIG. 1). The peak at 1.3 M $(NH_4)_2SO_4$ contained approximately 70% of the total OxDC and had a higher purity (>95%). OxDC from this peak was usually selected for the next step.

G-25 column for desalting. OxDC collected from the peak at 1.3 M $(NH_4)_2SO_4$ was loaded onto a G-25 sepharose containing column for desalting. Approximately 30 mg of purified OxDC was normally obtained from 10 grams of cell debris.

Example 2

Modification of OxDC Solubility to Increase Expression Level

OxDC has limited solubility at pH 4.5-7.8. The pH of *E. coli* cytoplasm is close to 7.6; thus, OxDC solubility in *E. coli* cytoplasm is very limited. In fact, it is observed that most OxDC expressed by *E. coli* is found in the lysed pellet rather than the supernatant.

Among the last 6 amino acid residues (residues 380-385) at the C-terminal tail of OxDC, there are four positively charged lysines, and two polar amino acids: serine and cysteine (Cys383). There are numerous amino acids to choose from to selectively replace cysteine or serine with side chains more or less polar. However, Cys383 which is the only cysteine residue residing in OxDC was selected. The three amino acids selected to replace cysteine were: arginine (R), serine (S) and alanine (A). The C383R, C383S and C383A mutants were created by standard site-directed mutagenesis and sequences of each gene was confirmed by DNA sequencing. The C383R, C383S and C383A mutants were expressed as described in Example 1 in 0.4 L scale shake flasks. *E. coli* cells were collected by centrifugation and lyzed by a standard protocol: *E. coli* cells were suspended in lysozyme solution and two cycles of freeze/thrawing. Complete lysis of *E. coli* cells was confirmed microscope analysis. Soluble and insoluble parts of these mutant enzymes were separated by centrifugation. Mutant enzymes in the insoluble pellets were extracted according to the method described in Example 1. The quantity of total mutant enzymes in the soluble part and the insoluble part (the extracted enzymes) were determined by activity assay and protein concentration. The purity of the extracted mutant enzymes was estimated from SDS-PAGE. The results of the 3 mutants and wild type enzyme are shown in Table 1.

The expression levels of wild type OxDC (C383C), C383R, C383S, and C383A mutants of OxDC and their distributions in the lysate (soluble form) and cell debris pellet (insoluble forms, but extracted) are shown below. The data were obtained from 6 grams of *E. coli* cell paste, which is equal to approximately 4 grams of lysed cell pellet, or 0.4 L of culture.

TABLE 1

The expression levels of wild type OxDC (C383), C383R, C383S, and C383A mutants of OxDC and their distributions in the lysate (soluble form) and cell debris pellet (insoluble form, but extracted).

| | OxDC in lysate (mg) | OxDC in pellet (mg) | Ratio of Soluble vs Insoluble | Total OxDC (mg) | Specific activity (U/mg) | Relative specific activity |
|---|---|---|---|---|---|---|
| C383R | 12 | 62 | 0.19 | 74 | 72 | 1.06 |
| C383 (Wild type) | 6.3 | 108 | 0.05 | 114 | 68 | 1 |
| C383S | 3.2 | 510 | 0.006 | 513 | 61 | 0.90 |
| C383A | 0 | 530 | 0 | 530 | 28 | 0.41 |

As shown in Table 1, mutating C383 altered the distribution of OxDC between soluble and insoluble fractions with the more polar side chain generating mutants with a higher ratio of soluble proteins in the lysate. The higher ratios of soluble proteins in the lysate correlated with lower expression level, but higher specific activity. The C383R mutant showed 6% higher specific activity than the wild type, but expression level was much lower. Although the C383A mutant OxDC showed a slightly higher expression than level than the C383S mutant, the specific activity was less than half of the C383S mutant. The C383S mutant expression level was approximately 5 times higher than the expression level of wild type OxDC and its specific activity was 90% as compared to wild type. The other properties of the C383S mutant enzyme were further characterized and compared with the wild type. Both the wild type and C383S mutant of OxDC are active between pH 3.5 and 5.5 with optimum activity at pH 4.0. Both enzymes are stable between pH 3.5 and 9.5 and at temperatures approaching 60° C. for at least 1 hr. In addition, the wild type showed at least two major peaks on a phenyl-sepharose column indicating more than one OxDC isoform, while the C383S mutant showed only one peak on the same column and under identical conditions (FIG. 1). The two isoforms of wild type OxDC introduces a more obstacles in terms of purification due to separation of two similar isoforms. For example, it may require a gradient elution on hydrophobic interaction chromatography column to separate the two isoforms. The two isoforms may also decrease the final yield of purified enzyme because more purification steps are required and each additional purification step results in losses in yield. In addition, one of the two isoforms may be useless.

Example 3

Alternative Expression System for the C383S Mutant

Construction of expression vectors. IPTG induction was compared with two other induction methods: rhamnose and temperature using a Lybradyn proprietary vector incorporated with the corresponding promotors. The results from small scale fermentation experiments indicated that all methods effectively expressed OxDC.

The vectors were constructed by standard molecular biological methods. The NdeI/BamHI fragment bearing the *E. coli* optimized YvrK gene was inserted into the NdeI/BamHI site of a Labradyn vector No. 101 under the control of the rhamnose-inducible promoter to create the plasmid pOTrhamC383S, which was transformed into *E. coli* BW25113 for OxDC production. The temperature-inducible vector pOTlprC383S was generated by replacing the rhamnose-induced promoter from pOTrhamC383S with a temperature induced promoter $\lambda_{PR}$ from phage lambda (lpr) carried by a Lybradyn vector No. 102 through MunI and AflII restriction sites. The expression vectors were later transformed into *E. coil* BW25113 for OxDC production. Other elements found in the vector include promoter and regulatory sequences, ribosome binding site, kanamycin/neomycin resistance, cer segregational stability element, and Rop plasmid copy number regulator sequences.

Comparison of expression level of the three expression vectors. Fermentation was performed in 200 mL flasks. The fermentation of OxDC by rhamnose induction was identical to IPTG induction as described in Example 1, except that 0.2% rhamnose was added at induction instead of 1.0 mM IPTG. The fermentation of OxDC by temperature induction was the same as IPTG and rhamnose induction except for two differences: *E. coil* was cultured at 30° C. instead of 37° C. and the induction was done by increasing the culture temperature to 42° C.

*E. coli* cells were harvested and lysed and OxDC was extracted from cell debris according to the methods described in Example 1. Both rhamnose and temperature induced expression systems yielded 400-600 mg of active C383S OxDC per liter of culture, a level close to IPTG expression (500 mg OxDC per liter of culture). Therefore, the temperature inducible expression system was selected.

Example 4

A Simple Purification Process with Solubility Adjustment by pH

Background. OxDC has limited solubility at pH 4.5-7.8 for the wild type and pH 4.0-8.0 for the C383S mutant. OxDC solubility increases if the pH is greater than 8.5 for the wild type OxDC and pH 9.0 for the C383S mutant. Tris and arginine are selective binding ligands to OxDC; therefore, both can greatly increase OxDC solubility. The purification process is applicable for the wild type and C383S mutant; however, only the C383S mutant is used to illustrate the purification method.

Step 1: extraction of C383S from cell debris pellet. All purification steps were performed at room temperature. Before extraction of C383S, *E. coli* cells were lyzed, cell debris was collected and washed with water to remove any soluble cell components according to the methods described in Example 1. However, the extraction of the OxDC from the cell debris here was different from Example 1. In Example 1, 0.75M $(NH_4)_2SO_4$ was added into 50 mM Tris buffer (pH 8.0) to extract OxDC from the pellet. In this method, extraction buffer was 50 mM Arginine or Tris HCl (pH 9.5) without addition of $(NH_4)_2SO_4$. The method was able to extract more of the C383S (>90% of total C383S in the pellet) mutant enzyme than the method described in Example 1 (75% of the total C383S mutant that was expressed) with much less host cell DNA and other impurities. The purity of C383S was usually greater than 99% (Table 2). In addition, the concentration of the C383S mutant OxDC in the extract reached 120 g/L, which reduced water use and also reduced the scale of the following step (Step 2).

Step 2: filtration. The majority of the impurities found in the extract were endotoxin which can be removed by two to three depth filters after addition of 0.6 M NaCl: the first filter was rated at 3 micron, the second 1.2 micron and finally the third depth filter was 0.2 or 0.1 micron. After filtration, the extract contained reduced levels of endotoxin (Table 2) and was ready for precipitation. If higher purity was required, one hydrophobic interaction chromatography (HIC) column was introduced for further processing before precipitation.

Step 3 (optional): HIC column. The filtrered C383S mutant OxDC solution was loaded onto an HIC column pre-equilibrated with 0.6 M NaCl in 50 mM Arg or Tris, pH 9.5. OxDC flowed through the column while impurities bound to the column which removed the impurites from the C383S solution. The C383S mutant flow through was collected for precipitation.

Step 3: precipitation by pH adjustment. For pH adjustment, 0.2 M citrate buffer, pH 3.0 was added dropwise to the C383S solution while stirring until the pH reached 7.0. The C383S mutant solubility dropped to less than 1 g/L at pH 7.0; thus, 99% of C383S (if starting concentration of the C383S mutant was 100 g/L) precipitates and was collected by centrifugation. The collected C383S mutant pellet may be washed 2-3 times to remove remaining NaCl, arginine or Tris by 50 mM citrate buffer, pH 6.0. The washed C383S pellet was in a very pure form (Table 2).

TABLE 2

Summary of a typical purification process starting with 5 kg of lysed cell pellet. The data in this table is the analysis results for the OxDC materials obtained at the end of each step.

| | Protein concentration (g/L) | Specific activity (U/mg protein) | Total amount protein (g) | Purity (SDS-PAGE) | DNA (ng/mg protein) | Endotoxin (EU/mg protein) |
|---|---|---|---|---|---|---|
| Extraction | 99 | 45.4 | 440 | 100 | 3.4 | 22000 |
| Filtration | 90 | 44.0 | 420 | 100 | 4.0 | 4000 |
| HIC | 60 | 44.3 | 360 | 100 | 4.1 | <0.5 |
| Precipitation | 50-100 | 44.6 | 350 | 100 | 3.7 | <0.5 |

Example 5

Spray Dry Dose Formulations (Particle Formation)

Process. All spray dry experiments were carried out with a Niro Moble Minor. Typical spray dry operation conditions are as follows: inlet temperature: 180-220° C., outlet temperature: 85-95° C., flow rate of dry air: 60-90 kg/h, atomization airflow: 8-15 kg/h, orifice diameter of the nozzle: 1-2 mm, feed flow rate: 1-4 kg/h. Table 3 summarizes compositions of different particle formulations according to this invention.

Results. Table 4 summarizes the specific activity of the C383S mutants in different spray dry particle formulations and in solution after redissolving the particles in phosphate buffer, pH 7.5. The polymer L 100-55 dissolved in water when pH is greater than 5.5. The control was the C383S mutant suspended in 50 mM citrate buffer without any protection from polymers, which lost 39% activity due to the high temperature and dehydration experienced during the spray dry process. The C383S mutant in formulations 1 and 2 was in solution and evenly distributed. The C383S mutant distribution in the outside layer of the spray dry microdrops might have inactivated during the spray dry process and thus resulted in 13% and 7% loss of activity, respectively. In contrast, the specific activity of the C383S mutant in formulations 3 to 8 were greater than formulation 1. When the structure of these particles is destroyed, for example, dissolving formulations 4-7 in 50 mM phosphate, pH 7.5, the specific activity returned to normal or even reduced levels as compared to free C383S, due to partial inactivation during spray drying.

Table 5 summarizes the stability data generated from these dry particles. Incubation at 45° C. for specified periods of time, showed excellent stability of formulations 1, 4 and 5.

Table 6 summarizes the results from in vitro pepsin protection testing. The particles were suspended in a pepsin (3.2 g/L)/acetate buffer. pH at 3.25, for 40 minutes at 37° C. while agitating at 1100 rpm. The remaining activity after treatment was measured by an activity assay. Formulation 1 did not give significant protection because it dissolved in water and destroyed the particle structure. Formulations 2 to 8 all showed protection from pepsin.

TABLE 3

Formulations that were tested by spray drying

Formulation 1  0.6% OxDC, 6% trehalose, 1.2% PVA and 1.2% Eudragit L100 in 12 mM arginine, pH 8.5
2  2% OxDC, 2% trehalose, 2% arginine and 3.9% Eudragit L100-55, pH 9.0
3  3% OxDC, 2% trehalose, 2.6% arginine and 4.5% Eudragit L100-55, pH 5.4

TABLE 3-continued

Formulations that were tested by spray drying

| Formulation | |
|---|---|
| 4 | The same as 2, except addition of 0.3% TEC |
| 5 | The same as 3 except without addition of arginine |
| 6 | 3% OxDC, 2% trehalose, 2.6% arginine, 0.3% TEC and 4.5% Eudragit FS30D, pH 5.4 |
| 7 | 3% OxDC, 2% trehalose, 2.6% arginine, 0.3% TEC and 4.5% Eudragit RS, pH 5.4 |
| 8 | 3% OxDC, 2% trehalose, 2.6% arginine, 0.3% TEC and 2.25% Eudragit RL and 2.25% Eudragit RS, pH 5.4 |

TABLE 4

The specific activity of C383S in spray drying particles and in the solutions after these particles were destructed by dissolving in phosphate buffer at pH 7.5.

| Test | C383S specific activity in particles (U/mg protein)$^B$ | C383S specific activity change (%) | C383S specific activity after particles dissolved (U/mg protein) |
|---|---|---|---|
| Free C383S | 45 | 100 | — |
| Control$^A$ | 27.5 | 61 | 27.0 |
| 1 | 39.2 | 87 | 39.4 |
| 2 | 48.9 | 93 | 48.5 |
| 3 | 57.2 | 127 | — |
| 4 | 63.5 | 141 | 44.3 |
| 5 | 55.8 | 124 | 42.6 |
| 6 | 46.8 | 104 | 41.7 |
| 7 | 57.2 | 127 | 43.0 |
| 8 | 57.2 | 127 | — |

$^A$Control: C383S suspended in 50 mM citrate buffer, pH 6.0, and spray dried under the same conditions.
$^B$Calculation of C383S specific activity: B/A. Here, A = the amount of C383S (mg) in 1 gram of solid mass of the feed; B = the total activity (U) in one gram of dry particles obtained from spray dry.

TABLE 5

The activity remaining after a certain period of incubation at 45° C.

| Test | 0 week | 1 week | 2 week | 4 week | 8 week | 12 week |
|---|---|---|---|---|---|---|
| Control | | | | | | |
| 1 | 36.1 | — | 37.6 | 40.0 | — | 41.6 |
| 2 | 42 | 35.9 | | | | |
| 3 | 57.2 | 44.2 | | | | |
| 4 | 63.5 | 52.2 | — | 65.3 | | |
| 5 | 54.9 | — | 51.4 | 47.2 | | |
| 6 | 46.8 | 29.1 | | | | |
| 7 | 57.1 | 3.2 | | | | |
| 8 | 57.1 | 42.5 | | | | |

TABLE 6

The activity after 40 min treated with 3.2 mg/ml pepsin solution at pH 3.25.

| Test | C383S activity remained (%) |
|---|---|
| Control | 22 |
| 1 | 30 |
| 2 | 72 |
| 3 | 75 |
| 4 | 82 |
| 5 | 80 |
| 6 | 89 |
| 7 | 77 |
| 8 | 79 |

Example 6

In Vivo Dose of Oxalate Reducing Particles

A 10-day study was conducted in male Sprague-Dawley rats. The purpose of this study was to evaluate the effects of administration of formulation 5 in Table 2 on the urinary response to oxalate loading in male Sprague-Dawley rats.

The study used 18 male Sprague-Dawley rats that were divided into 3 groups as shown in Table 7, which were administered oral doses of formulation 5 (Group 3) or vehicle (Group 2, control, 50 mM sodium citrate, pH 4.49) together with high oxalate diet. Group 1 was another control group, the 6 rats in this group were not administered a high oxalate diet, nor formulation 5. The rats were oral gavaged twice a day (BID). Rats in Group 3 received 500 U of formulation 5. After the rats were dosed, 30 minutes after the start of feeding, the rats were given access to food for an additional 1.5 hours in the morning (7:00-9:00 AM) and evening (3:30-5:30 PM). Food was weighed before the morning feeding and after both the morning and afternoon feedings. The rats were fed in their normal cages and immediately transferred to metabolic cages after dose administration on days—1, 4 and 9 in order to capture urine and fecal excretions.

Oxalate Determination

Quantitative oxalate determination from urine was determined by the colorimetric kit purchased from Trinity Biotech USA (St. Louis, Mo.). The assay is comprised of two enzymatic reactions as follows: (1) oxalate is oxidized to $CO_2$ and $H_2O_2$ by oxalate oxidase and (2) $H_2O_2$ reacts with 3-methyl-2-benzothiazolinone hydrazone (MBTH) and 3-(dimethylamino)benzoic acid (DMAB) in the presence of peroxidase to yield an indamine dye which can be detected at 590 nm. Urinary oxalate is calculated from a standard curve.

Creatinine Determination

Creatinine determination by LiquiColor® Procedure No. 0420. The creatinine colorimetric kit for the quantitative determination of creatinine in urine was purchased from StanBio Laboratory (Bocrne, Tex.). The assay is based on a modification of the automated reaction rate of Fabinay and Eringshausen method in which creatinine reacts with picric acid in alkaline conditions to form a color complex at 510 nm. The color development is directly proportional to the creatinine concentration. Urinary creatinine is calculated from a standard curve.

TABLE 7

Study Design

| Group | Diet | Dose | # of Rats | Days of dosing | Urinary oxalate excretion (Ox/Cr) |
|---|---|---|---|---|---|
| 1 | No Ox | 50 mM Citrate | 6 | 10 | |
| 2 | HOD | 50 mM Citrate | 6 | 10 | |
| 3 | HOD | Formulation 5 | 6 | 10 | |

HOD = High Oxalate Diet (Harlan Teklad TD04493)
No Ox = Harlan Teklad TD89222
Groups 1 and 2: 50 mM sodium citrate, pH 4.49
Group 3: formulation 5

Results

Figure 2:
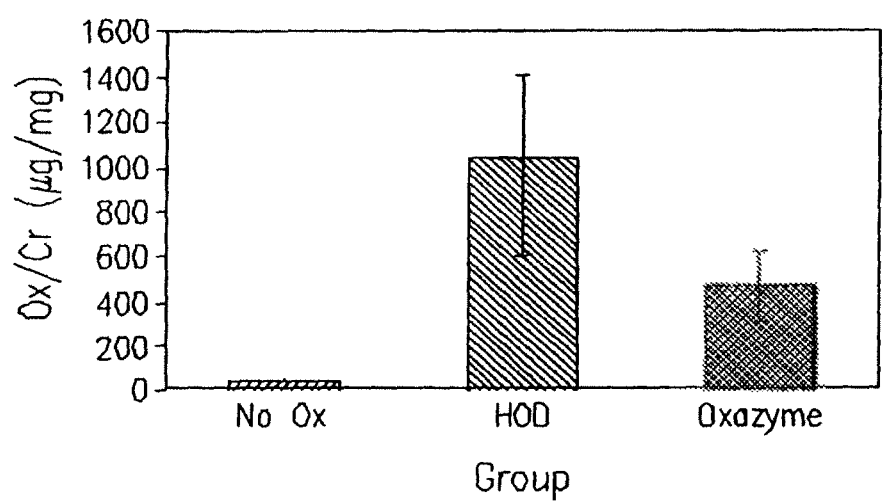
FIG. 2 is a graph showing mean urinary excretion of oxalate of rats fed 0 mg oxalate (baseline, no ox), 2.3% potassium oxalate (HOD) and oxalate decarboxylase particles of the present invention (Oxazyme) in conjunction with 2.3% potassium oxalate. Urinary oxalate is normalized against creatinine and is the accumulation of urine collected from days 4 and 9. Ox/Cr is Oxalate/creatinine.

Dosing formulation 5 with high oxalate diet significantly decreased urinary oxalate excretion of all six rats in group 3. On an average 500 U of formulation 5 fed with dietary oxalate was found to reduce urinary oxalate excretion by 49-59% (FIG. 2).

The invention claimed is:

1. Spray-dried particles comprising one or more isolated recombinant oxalate decarboxylase proteins encoded by the nucleotide sequence of SEQ ID NO:18, which are insoluble in the cytoplasm of a host cell and are not found as an inclusion body, and a polymeric material, wherein the activity of the one or more recombinant proteins at the most decreases to about 30% when incubated in a 3.2 mg/ml pepsin solution having a pH of about 3.2 for 40 minutes with the initial activity being set to 100%.

2. The particles of claim 1, wherein the polymeric material is a poly(meth)acrylate.

3. A composition comprising spray-dried particles as defined in claim 1.

4. The composition of claim 3, wherein the composition is an oral dosage form.

5. The composition of claim 4, wherein the oral dosage form is in a form selected from the group consisting of a sachet, tablet, capsule, chewable tablet, quick dissolve tablet, oral disintegrating tablet, liquid, syrup and elixir.

6. The spray-dried particles of claim 1, wherein the one or more recombinant oxalate decarboxylase proteins are isolated by a method comprising:
 (a) separating said one or more insoluble recombinant proteins not found as an inclusion body from soluble host cell proteins and
 (b) solubilising the separated one or more recombinant proteins.

7. The spray-dried particles of claim 6, wherein the method of isolating the recombinant oxalate decarboxylase proteins further comprises: (c) isolating the one or more solubilized recombinant proteins from the solubilising solution.

8. The spray-dried particles of claim 6, wherein the separating of the one or more recombinant proteins comprises centrifugation or filtration.

9. The spray-dried particles of claim 6, wherein the solubilising of the one or more recombinant proteins comprises adding binding ligands or providing a pH in which the one or more proteins are soluble.

10. The spray-dried particles of claim 7, wherein the isolating comprises precipitating the one or more recombinant proteins out of the solubilising solution.

11. The spray-dried particles of claim 10, the method of isolating the recombinant oxalate decarboxylase proteins further comprises washing the precipitated one or more recombinant proteins.

12. A method for making spray-dried particles according to claim 1, comprising one or more isolated recombinant oxalate decarboxylase proteins encoded by the nucleotide sequence of SEQ ID NO:18, which are insoluble in the cytoplasm of a host cell and are not found as an inclusion body, and a polymeric material, comprising
 isolating one or more recombinant oxalate decarboxylase proteins encoded by the nucleotide sequence of SEQ ID NO:18, that are insoluble in the cytoplasm of a host cell and are not found as an inclusion body, by a method comprising:
 (a) separating said one or more insoluble recombinant proteins not found as an inclusion body from soluble host cell proteins; and
 (b) solubilising the separated one or more recombinant proteins,
wherein the activity of the one or more recombinant proteins at the most decreases to about 30% when incubated in a 3.2 mg/ml pepsin solution having a pH of about 3.2 for 40 minutes with the initial activity being set to 100%.

13. The method of claim 12, further comprising, (c) isolating the one or more solubilized recombinant proteins from the solubilising solution.

14. The method of claim 12, wherein the separating of the one or more recombinant proteins comprises centrifugation or filtration.

15. The method of claim 12, wherein the solubilising of the one or more recombinant proteins comprises adding binding ligands or providing a pH in which the one or more proteins are soluble.

16. The method of claim 13, wherein the isolating comprises precipitating the one or more recombinant proteins out of the solubilising solution.

17. The method of claim 16, further comprising washing the precipitated one or more recombinant proteins.

18. A method for reducing absorption of oxalate, comprising orally administering to the stomach of a human or animal a composition comprising spray-dried particles according to claim 1.

19. The method of claim 18, wherein the human or animal is suffering from an oxalate-related condition selected from the group consisting of hyperoxaluria, absorptive hyperoxaluria, enteric hyperoxaluria, primary hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, post-gastrointestinal surgery conditions, post-bariatric surgery conditions, post-surgery for obesity conditions, and postantibiotic treatment.

20. A method for isolating one or more recombinant oxalate decarboxylase proteins encoded by the nucleotide sequence of SEQ ID NO:18, that are insoluble in the cytoplasm of a host cell and are not found as an inclusion body, comprising:
   (a) separating one or more insoluble recombinant proteins not found as an inclusion body from soluble host cell proteins; and
   (b) solubilising the separated one or more recombinant proteins,
   wherein the activity of the one or more recombinant proteins at the most decreases to about 30% when incubated in a 3.2 mg/ml pepsin solution having a pH of about 3.2 for 40 minutes with the initial activity being set to 100%.

* * * * *

SEQUENCE LISTING

<160> NUMBER OF SEQ ID NOS: 19

<210> SEQ ID NO 1
<211> LENGTH: 1152
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 1

| | | | | | |
|---|---|---|---|---|---|
| aaaaaacaaa | atgacattcc | gcagccaatt | agaggagaca | aaggagcaac | ggtaaaaatc | 60 |
| ccgcgcaata | ttgaaagaga | ccggcaaaac | cctgatatgc | tcgttccgcc | tgaaaccgat | 120 |
| catggcaccg | tcagcaatat | gaagttttca | ttctctgata | ctcataaccg | attagaaaaa | 180 |
| ggcggatatg | cccgggaagt | gacagtacgt | gaattgccga | tttcagaaaa | ccttgcatcc | 240 |
| gtaaatatgc | ggctgaagcc | aggcgcgatt | cgcgagcttc | actggcataa | agaagctgaa | 300 |
| tgggcttata | tgatttacgg | aagtgcaaga | gtcacaattg | tagatgaaaa | agggcgcagc | 360 |
| tttattgacg | atgtaggtga | aggagaccct | tggtacttcc | cgtcaggcct | gccgcactcc | 420 |
| atccaagcgc | tggaggaggg | agctgagttc | ctgctcgtgt | ttgacgatgg | atcattctct | 480 |
| gaaaacagca | cgttccagct | gacagattgg | ctggcccaca | ctccaaaaga | agtcattgct | 540 |
| gcgaacttcg | gcgtgacaaa | agaagagatt | tccaatttgc | ctggcaaaga | aaaatatata | 600 |
| tttgaaaacc | aacttcctgg | cagtttaaaa | gatgatattg | tggaagggcc | gaatggcgaa | 660 |
| gtgccttatc | catttactta | ccgccttctt | gaacaagagc | cgatcgaatc | tgagggagga | 720 |
| aaagtataca | ttgcagattc | gacaaacttc | aaagtgtcta | aaaccatcgc | atcagcgctc | 780 |
| gtaacagtag | aacccggcgc | catgagagaa | ctgcactggc | acccgaatac | ccacgaatgg | 840 |
| caatactaca | tctccggtaa | agctagaatg | accgttttg | catctgacgg | ccatgccaga | 900 |
| acgtttaatt | accaagccgg | tgatgtcgga | tatgtaccat | ttgcaatggg | tcattacgtt | 960 |
| gaaaacatcg | gggatgaacc | gcttgtcttt | ttagaaatct | tcaaagacga | ccattatgct | 1020 |
| gatgtatctt | taaccaatg | gcttgccatg | cttcctgaaa | catttgttca | agcgcacctt | 1080 |
| gacttgggca | aagactttac | tgatgtgctt | tcaaaagaaa | agcacccagt | agtgaaaaag | 1140 |
| aaatgcagta | aa | | | | | 1152 |

<210> SEQ ID NO 2
<211> LENGTH: 1164
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 2

| | | | | | |
|---|---|---|---|---|---|
| catatgaaaa | aacagaatga | cattccacag | ccgattcgcg | gcgataaagg | cgcgaccgtc | 60 |
| aaaattcctc | gcaatatcga | acgcgaccgc | cagaatccgg | atatgctggt | gccgccggag | 120 |
| acggaccatg | gcacggtgtc | taacatgaaa | ttctcttta | gcgatacccca | caaccgcctg | 180 |
| gaaaaaggtg | gctacgcgcg | cgaggttacc | gtccgtgaac | tgccaattag | cgaaaatctg | 240 |
| gcttcggtta | acatgcgtct | gaaaccaggt | gctatccgtg | agctgcactg | gcacaaggaa | 300 |
| gcggaatggg | cgtatatgat | ttacggttca | gcacgtgtta | ccatcgtaga | cgagaaaggt | 360 |
| cgtagcttta | tcgatgatgt | tggcgaaggt | gatctgtggt | atttcccatc | tggcctgccg | 420 |
| cattcgattc | aggcgctgga | agaaggcgct | gaatttctgc | tggtgttcga | tgatggttcc | 480 |

```
ttttctgaaa acagcacgtt ccagctgacg gattggctgg cgcacacgcc gaaagaagtc      540
attgcggcca attttggggt aaccaaagaa gaaatttcca acctgccggg caaagaaaag      600 tatattttg agaatcagct gccgggctct ctgaaggacg atattgtaga aggccctaac       660
ggtgaggtgc cgtatccgtt cacctatcgt ctgctggagc aggaaccgat tgaaagcgaa      720
ggcggtaaag tttatatcgc agattccact aactttaaag tctccaagac cattgccagc     780
gccctggtca ccgtggaacc gggagcgatg cgcgagctgc actggcatcc gaacacgcac     840
gaatggcagt attatatttc cggcaaagca cgcatgaccg ttttgcctc agatggacac      900 gctcgcacgt ttaattatca gcgggtgat gttggctacg ttcctttcgc catgggccat     960
tatgtagaaa atatcggcga tgaaccactg gtgtttctgg atctttaa agatgaccac      1020 tatgccgatg tttcactgaa tcagtggctg ccatgctgc cggaaacttt tgttcaggcg    1080
catctggacc tgggtaaaga ctttacggat gtgctgagca agaaaaaca cccggtagtc    1140 aagaagaaat gcagtaaagg atcc                                            1164
```

<210> SEQ ID NO 3
<211> LENGTH: 1152
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 3

```
aaaaaacaaa atgacattcc gcagccaatt agaggagaca aaggagcaac ggtaaaaatc      60
ccgcgcaata ttgaaagaga ccggcaaaac cctgatatgc tcgttccgcc tgaaaccgat     120
catggcaccg tcagcaatat gaagttttca ttctctgata ctcataaccg attagaaaaa     180
ggcggatatg cccgggaagt gacagtacgt gaattgccga tttcagaaaa ccttgcatcc     240
gtaaatatgc ggctgaagcc aggcgcgatt cgcgagcttc actggcataa agaagctgaa     300
tgggcttata tgatttacgg aagtgcaaga gtcacaattg tagatgaaaa agggcgcagc     360
tttattgacg atgtaggtga aggagacctt tggtacttcc cgtcaggcct gccgcactcc     420
atccaagcgc tggaggaggg agctgagttc ctgctcgtgt ttgacgatgg atcattctct     480
gaaaacagca cgttccagct gacagattgg ctggcccaca ctccaaaaga agtcattgct     540
gcgaacttcg gcgtgacaaa agaagagatt tccaatttgc ctggcaaaga aaatatata      600 tttgaaaacc aacttcctgg cagtttaaaa gatgatattg tggaagggcc gaatggcgaa     660
gtgccttatc catttactta ccgccttctt gaacaagagc cgatcgaatc tgagggagga     720
aaagtataca ttgcagattc gacaaacttc aaagtgtcta aaaccatcgc atcagcgctc     780
gtaacagtag aacccggcgc catgagagaa ctgcactggc acccgaatac ccacgaatgg     840
caatactaca tctccggtaa agctagaatg accgtttttg catctgacgg ccatgccaga     900
acgtttaatt accaagccgg tgatgtcgga tatgtaccat ttgcaatggg tcattacgtt     960
gaaaacatcg gggatgaacc gcttgtcttt ttagaaatct tcaaagacga ccattatgct    1020
gatgtatctt taaccaatg gcttgccatg cttcctgaaa catttgttca agcgcacctt    1080
gacttgggca aagactttac tgatgtgctt tcaaaagaaa agcacccagt agtgaaaaag    1140
aaatctagta aa                                                        1152
```

<210> SEQ ID NO 4
<211> LENGTH: 1152

<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 4

```
aaaaaacaaa atgacattcc gcagccaatt agaggagaca aaggagcaac ggtaaaaatc    60
ccgcgcaata ttgaaagaga ccggcaaaac cctgatatgc tcgttccgcc tgaaaccgat   120
catggcaccg tcagcaatat gaagttttca ttctctgata ctcataaccg attagaaaaa   180
ggcggatatg cccgggaagt gacagtacgt gaattgccga tttcagaaaa ccttgcatcc   240
gtaaatatgc ggctgaagcc aggcgcgatt cgcgagcttc actggcataa agaagctgaa   300
tgggcttata tgatttacgg aagtgcaaga gtcacaattg tagatgaaaa agggcgcagc   360
tttattgacg atgtaggtga aggagacctt tggtacttcc cgtcaggcct gccgcactcc   420
atccaagcgc tggaggaggg agctgagttc ctgctcgtgt tgacgatgg atcattctct   480
gaaaacagca cgttccagct gacagattgg ctggcccaca ctccaaaaga agtcattgct   540
gcgaacttcg gcgtgacaaa agaagagatt tccaatttgc ctggcaaaga aaatatata   600
tttgaaaacc aacttcctgg cagttttaaaa gatgatattg tggaagggcc gaatggcgaa   660
gtgccttatc catttactta ccgccttctt gaacaagagc cgatcgaatc tgagggagga   720
aaagtataca ttgcagattc gacaaacttc aaagtgtcta aaaccatcgc atcagcgctc   780
gtaacagtag aacccggcgc catgagagaa ctgcactggc acccgaatac ccacgaatgg   840
caatactaca tctccggtaa agctagaatg accgttttg catctgacgg ccatgccaga   900
acgtttaatt accaagccgg tgatgtcgga tatgtaccat ttgcaatggg tcattacgtt   960
gaaaacatcg gggatgaacc gcttgtcttt ttagaaatct tcaaagacga ccattatgct  1020
gatgtatctt taaaccaatg gcttgccatg cttcctgaaa catttgttca agcgcacctt  1080
gacttgggca aagactttac tgatgtgctt tcaaaagaaa agcacccagt agtgaaaaag  1140
aaatccagta aa                                                      1152
```

<210> SEQ ID NO 5
<211> LENGTH: 1152
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 5

```
aaaaaacaaa atgacattcc gcagccaatt agaggagaca aaggagcaac ggtaaaaatc    60
ccgcgcaata ttgaaagaga ccggcaaaac cctgatatgc tcgttccgcc tgaaaccgat   120
catggcaccg tcagcaatat gaagttttca ttctctgata ctcataaccg attagaaaaa   180
ggcggatatg cccgggaagt gacagtacgt gaattgccga tttcagaaaa ccttgcatcc   240
gtaaatatgc ggctgaagcc aggcgcgatt cgcgagcttc actggcataa agaagctgaa   300
tgggcttata tgatttacgg aagtgcaaga gtcacaattg tagatgaaaa agggcgcagc   360
tttattgacg atgtaggtga aggagacctt tggtacttcc cgtcaggcct gccgcactcc   420
atccaagcgc tggaggaggg agctgagttc ctgctcgtgt tgacgatgg atcattctct   480
gaaaacagca cgttccagct gacagattgg ctggcccaca ctccaaaaga agtcattgct   540
gcgaacttcg gcgtgacaaa agaagagatt tccaatttgc ctggcaaaga aaatatata   600
```

```
tttgaaaacc aacttcctgg cagtttaaaa gatgatattg tggaagggcc gaatggcgaa      660
gtgccttatc catttactta ccgccttctt gaacaagagc cgatcgaatc tgagggagga      720
aaagtataca ttgcagattc gacaaacttc aaagtgtcta aaaccatcgc atcagcgctc      780
gtaacagtag aacccggcgc catgagagaa ctgcactggc acccgaatac ccacgaatgg      840
caatactaca tctccggtaa agctagaatg accgttttg catctgacgg ccatgccaga       900
acgtttaatt accaagccgg tgatgtcgga tatgtaccat ttgcaatggg tcattacgtt      960
gaaaacatcg gggatgaacc gcttgtcttt ttagaaatct caaagacga ccattatgct      1020 gatgtatctt taaaccaatg gcttgccatg cttcctgaaa catttgttca agcgcacctt     1080
gacttgggca aagactttac tgatgtgctt tcaaaagaaa agcacccagt agtgaaaaag     1140
aaatcaagta aa                                                         1152
```

<210> SEQ ID NO 6
<211> LENGTH: 1140
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 6

```
aaaaaacaaa atgacattcc gcagccaatt agaggagaca aaggagcaac ggtaaaaatc       60
ccgcgcaata ttgaaagaga ccggcaaaac cctgatatgc tcgttccgcc tgaaaccgat      120
catggcaccg tcagcaatat gaagttttca ttctctgata ctcataaccg attagaaaaa      180
ggcggatatg cccgggaagt gacagtacgt gaattgccga tttcagaaaa ccttgcatcc      240
gtaaatatgc ggctgaagcc aggcgcgatt cgcgagcttc actggcataa agaagctgaa      300
tgggcttata tgatttacgg aagtgcaaga gtcacaattg tagatgaaaa agggcgcagc      360
tttattgacg atgtaggtga aggagaccct tggtacttcc cgtcaggcct gccgcactcc      420
atccaagcgc tggaggaggg agctgagttc ctgctcgtgt ttgacgatgg atcattctct      480
gaaaacagca cgttccagct gacagattgg ctggcccaca ctccaaaaga agtcattgct      540
gcgaacttcg gcgtgacaaa agaagagatt tccaatttgc ctggcaaaga aaatatata      600 tttgaaaacc aacttcctgg cagtttaaaa gatgatattg tggaagggcc gaatggcgaa      660
gtgccttatc catttactta ccgccttctt gaacaagagc cgatcgaatc tgagggagga      720
aaagtataca ttgcagattc gacaaacttc aaagtgtcta aaaccatcgc atcagcgctc      780
gtaacagtag aacccggcgc catgagagaa ctgcactggc acccgaatac ccacgaatgg      840
caatactaca tctccggtaa agctagaatg accgttttg catctgacgg ccatgccaga       900
acgtttaatt accaagccgg tgatgtcgga tatgtaccat ttgcaatggg tcattacgtt      960
gaaaacatcg gggatgaacc gcttgtcttt ttagaaatct caaagacga ccattatgct      1020 gatgtatctt taaaccaatg gcttgccatg cttcctgaaa catttgttca agcgcacctt     1080
gacttgggca aagactttac tgatgtgctt tcaaaagaaa agcacccagt agtgaaaaag     1140
```

<210> SEQ ID NO 7
<211> LENGTH: 1152
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 7

```
aaaaaacaaa atgacattcc gcagccaatt agaggagaca aaggagcaac ggtaaaaatc      60
ccgcgcaata ttgaaagaga ccggcaaaac cctgatatgc tcgttccgcc tgaaaccgat     120
catggcaccg tcagcaatat gaagttttca ttctctgata ctcataaccg attagaaaaa     180
ggcggatatg cccgggaagt gacagtacgt gaattgccga tttcagaaaa ccttgcatcc     240
gtaaatatgc ggctgaagcc aggcgcgatt cgcgagcttc actggcataa agaagctgaa     300
tgggcttata tgatttacgg aagtgcaaga gtcacaattg tagatgaaaa agggcgcagc     360
tttattgacg atgtaggtga aggagacctt tggtacttcc cgtcaggcct gccgcactcc     420
atccaagcgc tggaggaggg agctgagttc ctgctcgtgt ttgacgatgg atcattctct     480
gaaaacagca cgttccagct gacagattgg ctgcccaca  ctccaaaaga agtcattgct     540
gcgaacttcg gcgtgacaaa agaagagatt tccaatttgc ctggcaaaga aaaatatata     600
tttgaaaacc aacttcctgg cagtttaaaa gatgatattg tggaagggcc gaatggcgaa     660
gtgccttatc catttactta ccgccttctt gaacaagagc cgatcgaatc tgagggagga     720
aaagtataca ttgcagattc gacaaacttc aaagtgtcta aaaccatcgc atcagcgctc     780
gtaacagtag aacccggcgc catgagagaa ctgcactggc acccgaatac ccacgaatgg     840
caatactaca tctccggtaa agctagaatg accgttttg  catctgacgg ccatgccaga     900
acgtttaatt accaagccgg tgatgtcgga tatgtaccat ttgcaatggg tcattacgtt     960
gaaaacatcg gggatgaacc gcttgtcttt ttagaaatct tcaaagacga ccattatgct    1020
gatgtatctt taaccaatg gcttgccatg cttcctgaaa catttgttca agcgcacctt    1080
gacttgggca aagactttac tgatgtgctt tcaaaagaaa agcacccagt agtgaaaaag    1140
aaaagtagta aa                                                        1152
```

<210> SEQ ID NO 8
<211> LENGTH: 1152
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 8

```
aaaaaacaaa atgacattcc gcagccaatt agaggagaca aaggagcaac ggtaaaaatc      60
ccgcgcaata ttgaaagaga ccggcaaaac cctgatatgc tcgttccgcc tgaaaccgat     120
catggcaccg tcagcaatat gaagttttca ttctctgata ctcataaccg attagaaaaa     180
ggcggatatg cccgggaagt gacagtacgt gaattgccga tttcagaaaa ccttgcatcc     240
gtaaatatgc ggctgaagcc aggcgcgatt cgcgagcttc actggcataa agaagctgaa     300
tgggcttata tgatttacgg aagtgcaaga gtcacaattg tagatgaaaa agggcgcagc     360
tttattgacg atgtaggtga aggagacctt tggtacttcc cgtcaggcct gccgcactcc     420
atccaagcgc tggaggaggg agctgagttc ctgctcgtgt ttgacgatgg atcattctct     480
gaaaacagca cgttccagct gacagattgg ctgcccaca  ctccaaaaga agtcattgct     540
gcgaacttcg gcgtgacaaa agaagagatt tccaatttgc ctggcaaaga aaaatatata     600
tttgaaaacc aacttcctgg cagtttaaaa gatgatattg tggaagggcc gaatggcgaa     660
gtgccttatc catttactta ccgccttctt gaacaagagc cgatcgaatc tgagggagga     720
aaagtataca ttgcagattc gacaaacttc aaagtgtcta aaaccatcgc atcagcgctc     780
gtaacagtag aacccggcgc catgagagaa ctgcactggc acccgaatac ccacgaatgg     840
```

```
caatactaca tctccggtaa agctagaatg accgtttttg catctgacgg ccatgccaga      900
acgtttaatt accaagccgg tgatgtcgga tatgtaccat ttgcaatggg tcattacgtt      960
gaaaacatcg gggatgaacc gcttgtcttt ttagaaatct tcaaagacga ccattatgct     1020
gatgtatctt taaaccaatg gcttgccatg cttcctgaaa catttgttca agcgcacctt     1080
gacttgggca aagactttac tgatgtgctt tcaaaagaaa agcacccagt agtgaaaaag     1140
aaaagcagta aa                                                        1152

<210> SEQ ID NO 9
<211> LENGTH: 1152
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 9
aaaaaacaaa atgacattcc gcagccaatt agaggagaca aaggagcaac ggtaaaaatc       60
ccgcgcaata ttgaaagaga ccggcaaaac cctgatatgc tcgttccgcc tgaaaccgat      120
catggcaccg tcagcaatat gaagttttca ttctctgata ctcataaccg attagaaaaa      180
ggcggatatg cccgggaagt gacagtacgt gaattgccga tttcagaaaa ccttgcatcc      240
gtaaatatgc ggctgaagcc aggcgcgatt cgcgagcttc actggcataa gaagctgaa       300 tgggcttata tgatttacgg aagtgcaaga gtcacaattg tagatgaaaa agggcgcagc      360
tttattgacg atgtaggtga aggagacctt tggtacttcc cgtcaggcct gccgcactcc      420
atccaagcgc tggaggaggg agctgagttc ctgctcgtgt ttgacgatgg atcattctct      480
gaaaacagca cgttccagct gacagattgg ctggcccaca ctccaaaaga agtcattgct      540
gcgaacttcg gcgtgacaaa agaagagatt ccaatttgc ctggcaaaga aaatatata       600 tttgaaaacc aacttcctgg cagtttaaaa gatgatattg tggaagggcc gaatggcgaa      660
gtgccttatc catttactta ccgccttctt gaacaagagc cgatcgaatc tgagggagga      720
aaagtataca ttgcagattc gacaaacttc aaagtgtcta aaaccatcgc atcagcgctc      780
gtaacagtag aacccggcgc catgagagaa ctgcactggc acccgaatac ccacgaatgg      840
caatactaca tctccggtaa agctagaatg accgtttttg catctgacgg ccatgccaga      900
acgtttaatt accaagccgg tgatgtcgga tatgtaccat ttgcaatggg tcattacgtt      960
gaaaacatcg gggatgaacc gcttgtcttt ttagaaatct tcaaagacga ccattatgct     1020
gatgtatctt taaaccaatg gcttgccatg cttcctgaaa catttgttca agcgcacctt     1080
gacttgggca aagactttac tgatgtgctt tcaaaagaaa agcacccagt agtgaaaaag     1140
aaacgtagta aa                                                        1152

<210> SEQ ID NO 10
<211> LENGTH: 1152
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 10
aaaaaacaaa atgacattcc gcagccaatt agaggagaca aaggagcaac ggtaaaaatc       60
ccgcgcaata ttgaaagaga ccggcaaaac cctgatatgc tcgttccgcc tgaaaccgat      120
```

| | |
|---|---|
| catggcaccg tcagcaatat gaagttttca ttctctgata ctcataaccg attagaaaaa | 180 |
| ggcggatatg cccgggaagt gacagtacgt gaattgccga tttcagaaaa ccttgcatcc | 240 |
| gtaaatatgc ggctgaagcc aggcgcgatt cgcgagcttc actggcataa agaagctgaa | 300 |
| tgggcttata tgatttacgg aagtgcaaga gtcacaattg tagatgaaaa agggcgcagc | 360 |
| tttattgacg atgtaggtga aggagacctt tggtacttcc cgtcaggcct gccgcactcc | 420 |
| atccaagcgc tggaggaggg agctgagttc ctgctcgtgt ttgacgatgg atcattctct | 480 |
| gaaaacagca cgttccagct gacagattgg ctggcccaca ctccaaaaga agtcattgct | 540 |
| gcgaacttcg gcgtgacaaa agaagagatt tccaatttgc ctggcaaaga aaaatatata | 600 |
| tttgaaaacc aacttcctgg cagtttaaaa gatgatattg tggaagggcc gaatggcgaa | 660 |
| gtgccttatc catttactta ccgccttctt gaacaagagc cgatcgaatc tgagggagga | 720 |
| aaagtataca ttgcagattc gacaaacttc aaagtgtcta aaccatcgc atcagcgctc | 780 |
| gtaacagtag aacccggcgc catgagagaa ctgcactggc accgaatac ccacgaatgg | 840 |
| caatactaca tctccggtaa agctagaatg accgttttg catctgacgg ccatgccaga | 900 |
| acgtttaatt accaagccgg tgatgtcgga tatgtaccat ttgcaatggg tcattacgtt | 960 |
| gaaaacatcg gggatgaacc gcttgtcttt ttagaaatct tcaaagacga ccattatgct | 1020 |
| gatgtatctt taaaccaatg gcttgccatg cttcctgaaa catttgttca agcgcacctt | 1080 |
| gacttgggca agactttac tgatgtgctt tcaaagaaa agcacccagt agtgaaaaag | 1140 |
| aaacgcagta aa | 1152 |

<210> SEQ ID NO 11
<211> LENGTH: 1152
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 11

| | |
|---|---|
| aaaaaacaaa atgacattcc gcagccaatt agaggagaca aaggagcaac ggtaaaaatc | 60 |
| ccgcgcaata ttgaaagaga ccggcaaaac cctgatatgc tcgttccgcc tgaaaccgat | 120 |
| catggcaccg tcagcaatat gaagttttca ttctctgata ctcataaccg attagaaaaa | 180 |
| ggcggatatg cccgggaagt gacagtacgt gaattgccga tttcagaaaa ccttgcatcc | 240 |
| gtaaatatgc ggctgaagcc aggcgcgatt cgcgagcttc actggcataa agaagctgaa | 300 |
| tgggcttata tgatttacgg aagtgcaaga gtcacaattg tagatgaaaa agggcgcagc | 360 |
| tttattgacg atgtaggtga aggagacctt tggtacttcc cgtcaggcct gccgcactcc | 420 |
| atccaagcgc tggaggaggg agctgagttc ctgctcgtgt ttgacgatgg atcattctct | 480 |
| gaaaacagca cgttccagct gacagattgg ctggcccaca ctccaaaaga agtcattgct | 540 |
| gcgaacttcg gcgtgacaaa agaagagatt tccaatttgc ctggcaaaga aaaatatata | 600 |
| tttgaaaacc aacttcctgg cagtttaaaa gatgatattg tggaagggcc gaatggcgaa | 660 |
| gtgccttatc catttactta ccgccttctt gaacaagagc cgatcgaatc tgagggagga | 720 |
| aaagtataca ttgcagattc gacaaacttc aaagtgtcta aaccatcgc atcagcgctc | 780 |
| gtaacagtag aacccggcgc catgagagaa ctgcactggc accgaatac ccacgaatgg | 840 |
| caatactaca tctccggtaa agctagaatg accgttttg catctgacgg ccatgccaga | 900 |
| acgtttaatt accaagccgg tgatgtcgga tatgtaccat ttgcaatggg tcattacgtt | 960 |

-continued

```
gaaaacatcg gggatgaacc gcttgtcttt ttagaaatct tcaaagacga ccattatgct    1020
gatgtatctt taaaccaatg gcttgccatg cttcctgaaa catttgttca agcgcacctt    1080
gacttgggca aagactttac tgatgtgctt tcaaaagaaa agcacccagt agtgaaaaag    1140
aaacgaagta aa                                                        1152
```

<210> SEQ ID NO 12
<211> LENGTH: 1152
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 12

```
aaaaaacaaa atgacattcc gcagccaatt agaggagaca aaggagcaac ggtaaaaatc     60
ccgcgcaata ttgaaagaga ccggcaaaac cctgatatgc tcgttccgcc tgaaaccgat    120
catggcaccg tcagcaatat gaagttttca ttctctgata ctcataaccg attagaaaaa    180
ggcggatatg cccgggaagt gacagtacgt gaattgccga tttcagaaaa ccttgcatcc    240
gtaaatatgc ggctgaagcc aggcgcgatt cgcgagcttc actggcataa agaagctgaa    300
tgggcttata tgatttacgg aagtgcaaga gtcacaattg tagatgaaaa agggcgcagc    360
tttattgacg atgtaggtga aggagacctt tggtacttcc cgtcaggcct gccgcactcc    420
atccaagcgc tggaggaggg agctgagttc ctgctcgtgt ttgacgatgg atcattctct    480
gaaaacagca cgttccagct gacagattgg ctggcccaca ctccaaaaga agtcattgct    540
gcgaacttcg gcgtgacaaa agaagagatt tccaatttgc ctggcaaaga aaatatata     600 tttgaaaacc aacttcctgg cagtttaaaa gatgatattg tggaagggcc gaatggcgaa    660
gtgccttatc catttactta ccgccttctt gaacaagagc cgatcgaatc tgagggagga    720
aaagtataca ttgcagattc gacaaacttc aaagtgtcta aaaccatcgc atcagcgctc    780
gtaacagtag aacccggcgc catgagagaa ctgcactggc acccgaatac ccacgaatgg    840
caatactaca tctccggtaa agctagaatg accgtttttg catctgacgg ccatgccaga    900
acgtttaatt accaagccgg tgatgtcgga tatgtaccat ttgcaatggg tcattacgtt    960
gaaaacatcg gggatgaacc gcttgtcttt ttagaaatct tcaaagacga ccattatgct   1020
gatgtatctt taaaccaatg gcttgccatg cttcctgaaa catttgttca agcgcacctt   1080
gacttgggca aagactttac tgatgtgctt tcaaaagaaa agcacccagt agtgaaaaag   1140
aaacggagta aa                                                       1152
```

<210> SEQ ID NO 13
<211> LENGTH: 1152
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 13

```
aaaaaacaaa atgacattcc gcagccaatt agaggagaca aaggagcaac ggtaaaaatc     60
ccgcgcaata ttgaaagaga ccggcaaaac cctgatatgc tcgttccgcc tgaaaccgat    120
catggcaccg tcagcaatat gaagttttca ttctctgata ctcataaccg attagaaaaa    180
ggcggatatg cccgggaagt gacagtacgt gaattgccga tttcagaaaa ccttgcatcc    240
gtaaatatgc ggctgaagcc aggcgcgatt cgcgagcttc actggcataa agaagctgaa    300
```

```
tgggcttata tgatttacgg aagtgcaaga gtcacaattg tagatgaaaa agggcgcagc      360
tttattgacg atgtaggtga aggagacctt tggtacttcc cgtcaggcct gccgcactcc      420
atccaagcgc tggaggaggg agctgagttc ctgctcgtgt ttgacgatgg atcattctct      480
gaaaacagca cgttccagct gacagattgg ctggcccaca ctccaaaaga agtcattgct      540
gcgaacttcg gcgtgacaaa agaagagatt tccaatttgc ctggcaaaga aaatatata      600 tttgaaaacc aacttcctgg cagtttaaaa gatgatattg tggaagggcc gaatggcgaa      660
gtgccttatc catttactta ccgccttctt gaacaagagc cgatcgaatc tgagggagga      720
aaagtataca ttgcagattc gacaaacttc aaagtgtcta aaaccatcgc atcagcgctc      780
gtaacagtag aacccggcgc catgagagaa ctgcactggc acccgaatac ccacgaatgg      840
caatactaca tctccggtaa agctagaatg accgtttttg catctgacgg ccatgccaga      900
acgtttaatt accaagccgg tgatgtcgga tatgtaccat ttgcaatggg tcattacgtt      960
gaaaacatcg gggatgaacc gcttgtcttt ttagaaatct tcaaagacga ccattatgct     1020
gatgtatctt taaaccaatg gcttgccatg cttcctgaaa catttgttca agcgcacctt     1080
gacttgggca aagactttac tgatgtgctt tcaaaagaaa agcacccagt agtgaaaaag     1140
aaaagaagta aa                                                          1152

<210> SEQ ID NO 14
<211> LENGTH: 1152
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 14
aaaaaacaaa atgacattcc gcagccaatt agaggagaca aaggagcaac ggtaaaaatc       60
ccgcgcaata ttgaaagaga ccggcaaaac cctgatatgc tcgttccgcc tgaaaccgat      120
catggcaccg tcagcaatat gaagttttca ttctctgata ctcataaccg attagaaaaa      180
ggcggatatg cccgggaagt gacagtacgt gaattgccga tttcagaaaa ccttgcatcc      240
gtaaatatgc ggctgaagcc aggcgcgatt cgcgagcttc actggcataa agaagctgaa      300
tgggcttata tgatttacgg aagtgcaaga gtcacaattg tagatgaaaa agggcgcagc      360
tttattgacg atgtaggtga aggagacctt tggtacttcc cgtcaggcct gccgcactcc      420
atccaagcgc tggaggaggg agctgagttc ctgctcgtgt ttgacgatgg atcattctct      480
gaaaacagca cgttccagct gacagattgg ctggcccaca ctccaaaaga agtcattgct      540
gcgaacttcg gcgtgacaaa agaagagatt tccaatttgc ctggcaaaga aaatatata      600 tttgaaaacc aacttcctgg cagtttaaaa gatgatattg tggaagggcc gaatggcgaa      660
gtgccttatc catttactta ccgccttctt gaacaagagc cgatcgaatc tgagggagga      720
aaagtataca ttgcagattc gacaaacttc aaagtgtcta aaaccatcgc atcagcgctc      780
gtaacagtag aacccggcgc catgagagaa ctgcactggc acccgaatac ccacgaatgg      840
caatactaca tctccggtaa agctagaatg accgtttttg catctgacgg ccatgccaga      900
acgtttaatt accaagccgg tgatgtcgga tatgtaccat ttgcaatggg tcattacgtt      960
gaaaacatcg gggatgaacc gcttgtcttt ttagaaatct tcaaagacga ccattatgct     1020
gatgtatctt taaaccaatg gcttgccatg cttcctgaaa catttgttca agcgcacctt     1080
gacttgggca aagactttac tgatgtgctt tcaaaagaaa agcacccagt agtgaaaaag     1140
```
aaaaggagta aa                                                     1152

<210> SEQ ID NO 15
<211> LENGTH: 1152
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 15
aaaaaacaaa atgacattcc gcagccaatt agaggagaca aaggagcaac ggtaaaaatc    60
ccgcgcaata ttgaaagaga ccggcaaaac cctgatatgc tcgttccgcc tgaaaccgat   120
catggcaccg tcagcaatat gaagttttca ttctctgata ctcataaccg attagaaaaa   180
ggcggatatg cccgggaagt gacagtacgt gaattgccga tttcagaaaa ccttgcatcc   240
gtaaatatgc ggctgaagcc aggcgcgatt cgcgagcttc actggcataa agaagctgaa   300
tgggcttata tgatttacgg aagtgcaaga gtcacaattg tagatgaaaa agggcgcagc   360
tttattgacg atgtaggtga aggagacctt tggtacttcc cgtcaggcct gccgcactcc   420
atccaagcgc tggaggaggg agctgagttc ctgctcgtgt tgacgatgg atcattctct    480
gaaacagca cgttccagct gacagattgg ctggcccaca ctccaaaaga agtcattgct    540
gcgaacttcg gcgtgacaaa agaagagatt tccaatttgc ctggcaaaga aaatatata    600
tttgaaaacc aacttcctgg cagtttaaaa gatgatattg tggaagggcc gaatggcgaa   660
gtgccttatc catttactta ccgccttctt gaacaagagc cgatcgaatc tgagggagga   720
aaagtataca ttgcagattc gacaaacttc aaagtgtcta aaaccatcgc atcagcgctc   780
gtaacagtag aacccggcgc catgagagaa ctgcactggc accgaatac ccacgaatgg    840
caatactaca tctccggtaa agctagaatg accgttttg catctgacgg ccatgccaga    900
acgtttaatt accaagccgg tgatgtcgga tatgtaccat ttgcaatggg tcattacgtt   960
gaaaacatcg gggatgaacc gcttgtcttt ttagaaatct tcaaagacga ccattatgct  1020
gatgtatctt taaaccaatg gcttgccatg cttcctgaaa catttgttca agcgcacctt  1080
gacttgggca aagactttac tgatgtgctt tcaaaagaaa agcacccagt agtgaaaaag  1140
aaagctagta aa                                                     1152

<210> SEQ ID NO 16
<211> LENGTH: 1152
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 16
aaaaaacaaa atgacattcc gcagccaatt agaggagaca aaggagcaac ggtaaaaatc    60
ccgcgcaata ttgaaagaga ccggcaaaac cctgatatgc tcgttccgcc tgaaaccgat   120
catggcaccg tcagcaatat gaagttttca ttctctgata ctcataaccg attagaaaaa   180
ggcggatatg cccgggaagt gacagtacgt gaattgccga tttcagaaaa ccttgcatcc   240
gtaaatatgc ggctgaagcc aggcgcgatt cgcgagcttc actggcataa agaagctgaa   300
tgggcttata tgatttacgg aagtgcaaga gtcacaattg tagatgaaaa agggcgcagc   360
tttattgacg atgtaggtga aggagacctt tggtacttcc cgtcaggcct gccgcactcc   420

```
atccaagcgc tggaggaggg agctgagttc ctgctcgtgt tgacgatgg atcattctct      480 gaaaacagca cgttccagct gacagattgg ctggcccaca ctccaaaaga agtcattgct    540
gcgaacttcg gcgtgacaaa agaagagatt ccaatttgc ctggcaaaga aaaatatata     600
tttgaaaacc aacttcctgg cagtttaaaa gatgatattg tggaagggcc gaatggcgaa    660
gtgccttatc catttactta ccgccttctt gaacaagagc cgatcgaatc tgagggagga    720
aaagtataca ttgcagattc gacaaacttc aaagtgtcta aaaccatcgc atcagcgctc    780
gtaacagtag aacccggcgc catgagagaa ctgcactggc acccgaatac ccacgaatgg    840
caatactaca tctccggtaa agctagaatg accgttttg catctgacgg ccatgccaga     900
acgtttaatt accaagccgg tgatgtcgga tatgtaccat ttgcaatggg tcattacgtt    960
gaaaacatcg gggatgaacc gcttgtcttt ttagaaatct tcaaagacga ccattatgct   1020
gatgtatctt taaaccaatg gcttgccatg cttcctgaaa catttgttca agcgcacctt   1080
gacttgggca aagactttac tgatgtgctt tcaaaagaaa agcacccagt agtgaaaaag   1140
aaagccagta aa                                                      1152

<210> SEQ ID NO 17
<211> LENGTH: 1152
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 17
aaaaaacaaa atgacattcc gcagccaatt agaggagaca aaggagcaac ggtaaaaatc     60
ccgcgcaata ttgaaagaga ccggcaaaac cctgatatgc tcgttccgcc tgaaaccgat    120
catggcaccg tcagcaatat gaagttttca ttctctgata ctcataaccg attagaaaaa    180
ggcggatatg cccgggaagt gacagtacgt gaattgccga tttcagaaaa ccttgcatcc    240
gtaaatatgc ggctgaagcc aggcgcgatt cgcgagcttc actggcataa agaagctgaa    300
tgggcttata tgatttacgg aagtgcaaga gtcacaattg tagatgaaaa agggcgcagc    360
tttattgacg atgtaggtga aggagacctt tggtacttcc cgtcaggcct gccgcactcc    420
atccaagcgc tggaggaggg agctgagttc ctgctcgtgt tgacgatgg atcattctct    480 gaaaacagca cgttccagct gacagattgg ctggcccaca ctccaaaaga agtcattgct    540
gcgaacttcg gcgtgacaaa agaagagatt ccaatttgc ctggcaaaga aaaatatata     600
tttgaaaacc aacttcctgg cagtttaaaa gatgatattg tggaagggcc gaatggcgaa    660
gtgccttatc catttactta ccgccttctt gaacaagagc cgatcgaatc tgagggagga    720
aaagtataca ttgcagattc gacaaacttc aaagtgtcta aaaccatcgc atcagcgctc    780
gtaacagtag aacccggcgc catgagagaa ctgcactggc acccgaatac ccacgaatgg    840
caatactaca tctccggtaa agctagaatg accgttttg catctgacgg ccatgccaga     900
acgtttaatt accaagccgg tgatgtcgga tatgtaccat ttgcaatggg tcattacgtt    960
gaaaacatcg gggatgaacc gcttgtcttt ttagaaatct tcaaagacga ccattatgct   1020
gatgtatctt taaaccaatg gcttgccatg cttcctgaaa catttgttca agcgcacctt   1080
gacttgggca aagactttac tgatgtgctt tcaaaagaaa agcacccagt agtgaaaaag   1140
aaagcaagta aa                                                      1152

<210> SEQ ID NO 18
```

<211> LENGTH: 1152
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 18

| | | |
|---|---|---|
| aaaaaacaaa atgacattcc gcagccaatt agaggagaca aaggagcaac ggtaaaaatc | 60 |
| ccgcgcaata ttgaaagaga ccggcaaaac cctgatatgc tcgttccgcc tgaaaccgat | 120 |
| catggcaccg tcagcaatat gaagttttca ttctctgata ctcataaccg attagaaaaa | 180 |
| ggcggatatg cccgggaagt gacagtacgt gaattgccga tttcagaaaa ccttgcatcc | 240 |
| gtaaatatgc ggctgaagcc aggcgcgatt cgcgagcttc actggcataa agaagctgaa | 300 |
| tgggcttata tgatttacgg aagtgcaaga gtcacaattg tagatgaaaa agggcgcagc | 360 |
| tttattgacg atgtaggtga aggagacctt tggtacttcc cgtcaggcct gccgcactcc | 420 |
| atccaagcgc tggaggaggg agctgagttc ctgctcgtgt ttgacgatgg atcattctct | 480 |
| gaaaacagca cgttccagct gacagattgg ctggcccaca ctccaaaaga agtcattgct | 540 |
| gcgaacttcg gcgtgacaaa agaagagatt tccaatttgc ctggcaaaga aaatatata | 600 |
| tttgaaaacc aacttcctgg cagtttaaaa gatgatattg tggaagggcc gaatggcgaa | 660 |
| gtgccttatc catttactta ccgccttctt gaacaagagc cgatcgaatc tgagggagga | 720 |
| aaagtataca ttgcagattc gacaaacttc aaagtgtcta aaaccatcgc atcagcgctc | 780 |
| gtaacagtag aacccggcgc catgagagaa ctgcactggc acccgaatac ccacgaatgg | 840 |
| caatactaca tctccggtaa agctagaatg accgttttg catctgacgg ccatgccaga | 900 |
| acgtttaatt accaagccgg tgatgtcgga tatgtaccat ttgcaatggg tcattacgtt | 960 |
| gaaaacatcg gggatgaacc gcttgtcttt ttagaaatct tcaaagacga ccattatgct | 1020 |
| gatgtatctt taaaccaatg gcttgccatg cttcctgaaa catttgttca agcgcacctt | 1080 |
| gacttgggca aagactttac tgatgtgctt tcaaaagaaa agcacccagt agtgaaaaag | 1140 |
| aaagcgagta aa | 1152 |

<210> SEQ ID NO 19
<211> LENGTH: 1152
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 19

| | | |
|---|---|---|
| aaaaaacaaa atgacattcc gcagccaatt agaggagaca aaggagcaac ggtaaaaatc | 60 |
| ccgcgcaata ttgaaagaga ccggcaaaac cctgatatgc tcgttccgcc tgaaaccgat | 120 |
| catggcaccg tcagcaatat gaagttttca ttctctgata ctcataaccg attagaaaaa | 180 |
| ggcggatatg cccgggaagt gacagtacgt gaattgccga tttcagaaaa ccttgcatcc | 240 |
| gtaaatatgc ggctgaagcc aggcgcgatt cgcgagcttc actggcataa agaagctgaa | 300 |
| tgggcttata tgatttacgg aagtgcaaga gtcacaattg tagatgaaaa agggcgcagc | 360 |
| tttattgacg atgtaggtga aggagacctt tggtacttcc cgtcaggcct gccgcactcc | 420 |
| atccaagcgc tggaggaggg agctgagttc ctgctcgtgt ttgacgatgg atcattctct | 480 |
| gaaaacagca cgttccagct gacagattgg ctggcccaca ctccaaaaga agtcattgct | 540 |
| gcgaacttcg gcgtgacaaa agaagagatt tccaatttgc ctggcaaaga aaatatata | 600 |

```
tttgaaaacc aacttcctgg cagtttaaaa gatgatattg tggaagggcc gaatggcgaa    660
gtgccttatc catttactta ccgccttctt gaacaagagc cgatcgaatc tgagggagga    720
aaagtataca ttgcagattc gacaaacttc aaagtgtcta aaaccatcgc atcagcgctc    780
gtaacagtag aacccggcgc catgagagaa ctgcactggc acccgaatac ccacgaatgg    840
caatactaca tctccggtaa agctagaatg accgttttg catctgacgg ccatgccaga     900
acgtttaatt accaagccgg tgatgtcgga tatgtaccat ttgcaatggg tcattacgtt    960
gaaaacatcg gggatgaacc gcttgtcttt ttagaaatct tcaaagacga ccattatgct   1020
gatgtatctt taaaccaatg gcttgccatg cttcctgaaa catttgttca agcgcacctt   1080
gacttgggca aagactttac tgatgtgctt tcaaaagaaa agcacccagt agtgaaaaag   1140
aaaggaagta aa                                                       1152
```